United States Patent
Evans et al.

(10) Patent No.: US 7,938,767 B2
(45) Date of Patent: May 10, 2011

(54) SYSTEMS AND METHODS FOR VOLUME REDUCTION

(75) Inventors: Michael A. Evans, Palo Alto, CA (US); Gwendolyn A. Watanabe, Sunnyvale, CA (US)

(73) Assignee: Northwind Ventures, Sunnyvale, CA (US)

( * ) Notice: Subject to any disclaimer, the term of this patent is extended or adjusted under 35 U.S.C. 154(b) by 358 days.

(21) Appl. No.: 12/187,287

(22) Filed: Aug. 6, 2008

(65) Prior Publication Data
US 2008/0293996 A1  Nov. 27, 2008

Related U.S. Application Data

(63) Continuation of application No. PCT/US2007/061679, filed on Feb. 6, 2007.

(60) Provisional application No. 60/765,158, filed on Feb. 6, 2006.

(51) Int. Cl.
*A61M 1/10* (2006.01)
(52) U.S. Cl. .................................................. 600/16
(58) Field of Classification Search .............. 600/16, 600/37, 17–18
See application file for complete search history.

(56) References Cited

U.S. PATENT DOCUMENTS

| | | |
|---|---|---|
| 5,551,435 A | 9/1996 | Sramek |
| 6,125,852 A | 10/2000 | Stevens et al. |
| 6,221,104 B1 | 4/2001 | Buckberg et al. |
| 6,230,714 B1 | 5/2001 | Alferness et al. |
| 6,360,749 B1 | 3/2002 | Jayaraman |
| 6,450,171 B1 | 9/2002 | Buckberg et al. |
| 6,482,146 B1 | 11/2002 | Alferness et al. |
| 6,508,756 B1 | 1/2003 | Kung et al. |
| 6,537,198 B1 | 3/2003 | Vidlund et al. |
| 6,547,821 B1 | 4/2003 | Taylor et al. |
| 6,586,414 B2 | 7/2003 | Haque et al. |
| 6,622,730 B2 | 9/2003 | Ekvall et al. |
| 6,682,476 B2 | 1/2004 | Alferness et al. |
| 6,685,627 B2 | 2/2004 | Jayaraman |
| 6,802,319 B2 | 10/2004 | Stevens et al. |
| 6,852,076 B2 | 2/2005 | Nikolic et al. |
| 6,861,439 B2 | 3/2005 | Haque et al. |

(Continued)

FOREIGN PATENT DOCUMENTS

WO   WO 96/37859 A1   11/1996

(Continued)

OTHER PUBLICATIONS

Sharkey, Hugh et al., "Left Ventricular Apex Occluder. Description of a Ventricular Partitioning Device," *EuroIntev.*, 2:125-127, 2006.

*Primary Examiner* — Scott M Getzow
*Assistant Examiner* — Amanda Patton
(74) *Attorney, Agent, or Firm* — Levine Bagade Han LLP

(57) ABSTRACT

Systems and methods are provided for reducing the effective volume of a cardiac ventricle. A ventricular volume reduction system may include a containment system or container body deliverable through a catheter into the ventricle, with the containment system or container body being fillable to occupy space within the ventricle. A ventricular volume reduction system may include a partition that sequesters a portion of the ventricle and separates it from the flow path of blood in the ventricle. Methods for reducing the effective ventricular chamber volume may include placement of the containment system, the container body or the partition within the ventricle.

21 Claims, 17 Drawing Sheets

U.S. PATENT DOCUMENTS

| | | |
|---|---|---|
| 6,902,524 B2 | 6/2005 | Alferness et al. |
| 6,951,534 B2 | 10/2005 | Girard et al. |
| 7,303,526 B2 | 12/2007 | Sharkey et al. |
| 2002/0029783 A1 | 3/2002 | Stevens et al. |
| 2002/0056461 A1 | 5/2002 | Jayaraman |
| 2002/0169360 A1 | 11/2002 | Taylor et al. |
| 2002/0188170 A1 | 12/2002 | Santamore et al. |
| 2003/0045776 A1 | 3/2003 | Alferness et al. |
| 2003/0050529 A1 | 3/2003 | Vidlund et al. |
| 2003/0050682 A1 | 3/2003 | Sharkey et al. |
| 2003/0078465 A1 | 4/2003 | Pai et al. |
| 2003/0078671 A1 | 4/2003 | Lesniak et al. |
| 2003/0088151 A1 | 5/2003 | Kung et al. |
| 2003/0102000 A1 | 6/2003 | Stevens et al. |
| 2003/0229265 A1 | 12/2003 | Girard et al. |
| 2004/0002626 A1 | 1/2004 | Feld et al. |
| 2004/0015046 A1 | 1/2004 | Buckberg et al. |
| 2004/0044361 A1 | 3/2004 | Frazier et al. |
| 2004/0055608 A1 | 3/2004 | Stevens et al. |
| 2004/0098031 A1 | 5/2004 | van der Burg et al. |
| 2004/0102679 A1 | 5/2004 | Alferness et al. |
| 2004/0122090 A1 | 6/2004 | Lipton |
| 2004/0133062 A1 | 7/2004 | Pai et al. |
| 2004/0136992 A1 | 7/2004 | Burton et al. |
| 2004/0158123 A1 | 8/2004 | Jayaraman |
| 2004/0181126 A1 | 9/2004 | Buckberg et al. |
| 2004/0215230 A1 | 10/2004 | Frazier et al. |
| 2004/0230222 A1 | 11/2004 | van der Burg et al. |
| 2004/0260346 A1 | 12/2004 | Overall et al. |
| 2004/0267086 A1 | 12/2004 | Anstadt et al. |
| 2005/0043708 A1 | 2/2005 | Gleeson et al. |
| 2005/0080402 A1 | 4/2005 | Santamore et al. |
| 2005/0085688 A1 | 4/2005 | Girard et al. |
| 2005/0119519 A9 | 6/2005 | Girard et al. |
| 2005/0124849 A1 | 6/2005 | Barbut et al. |
| 2005/0142180 A1 | 6/2005 | Bisgaier et al. |
| 2005/0154252 A1* | 7/2005 | Sharkey et al. .................. 600/37 |
| 2005/0177180 A1 | 8/2005 | Kaganov et al. |
| 2005/0187620 A1 | 8/2005 | Pai et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0197716 A1* | 9/2005 | Sharkey et al. ............ 623/23.67 |
| 2005/0228217 A1 | 10/2005 | Alferness et al. |
| 2005/0234289 A1 | 10/2005 | Anstadt et al. |
| 2005/0277981 A1 | 12/2005 | Maahs et al. |
| 2005/0277983 A1 | 12/2005 | Saadat et al. |
| 2006/0014998 A1 | 1/2006 | Sharkey et al. |
| 2006/0019888 A1 | 1/2006 | Zhou |
| 2006/0025800 A1 | 2/2006 | Suresh |
| 2006/0079736 A1 | 4/2006 | Chin et al. |
| 2006/0206148 A1 | 9/2006 | Khairkhahan et al. |
| 2006/0229491 A1 | 10/2006 | Sharkey et al. |
| 2006/0264980 A1 | 11/2006 | Khairkhahan et al. |
| 2006/0281965 A1 | 12/2006 | Khairkhahan et al. |
| 2007/0161846 A1 | 7/2007 | Nikolic et al. |
| 2007/0213578 A1 | 9/2007 | Khairkhahan et al. |
| 2007/0213815 A1 | 9/2007 | Khairkhahan et al. |
| 2008/0071298 A1 | 3/2008 | Khairkhahan et al. |

FOREIGN PATENT DOCUMENTS

| | | |
|---|---|---|
| WO | WO 98/03213 A1 | 1/1998 |
| WO | WO 00/28912 A1 | 5/2000 |
| WO | WO 00/42919 A1 | 7/2000 |
| WO | WO 00/50639 A2 | 8/2000 |
| WO | WO 01/70116 A1 | 9/2001 |
| WO | WO 01/95830 A2 | 12/2001 |
| WO | WO 02/45710 A1 | 6/2002 |
| WO | WO 02/087481 A1 | 11/2002 |
| WO | WO 03/043507 A2 | 5/2003 |
| WO | WO 03/043507 A3 | 5/2003 |
| WO | WO 03/063691 A2 | 8/2003 |
| WO | WO 03/090716 A1 | 11/2003 |
| WO | WO 03/099300 A1 | 12/2003 |
| WO | WO 03/099320 A1 | 12/2003 |
| WO | WO 03/103538 A1 | 12/2003 |
| WO | WO 03/103743 A2 | 12/2003 |
| WO | WO 2004/019866 A2 | 3/2004 |
| WO | WO 2004/066805 A2 | 8/2004 |
| WO | WO 2004/066825 A2 | 8/2004 |
| WO | WO 2005/000160 A2 | 1/2005 |
| WO | WO 2005/041745 A2 | 5/2005 |
| WO | WO 2005/041866 A2 | 5/2005 |
| WO | WO 2005/046520 A2 | 5/2005 |
| WO | WO 2005/091860 A2 | 10/2005 |
| WO | WO 2005/102181 A1 | 11/2005 |
| WO | WO 2006/033107 A2 | 3/2006 |
| WO | WO 2006/044467 A2 | 4/2006 |

* cited by examiner

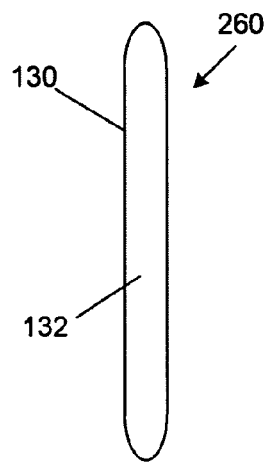 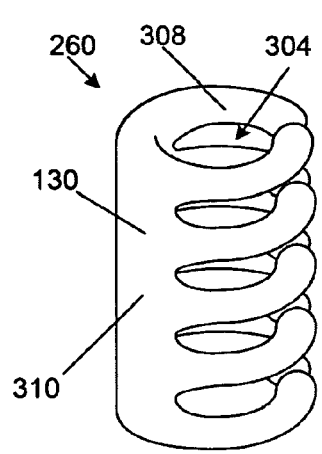 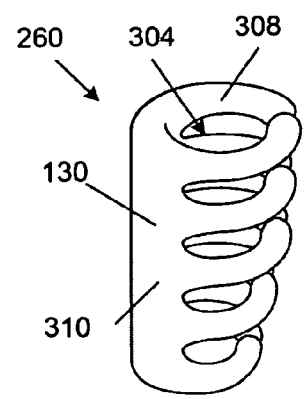
Fig. 14    Fig. 15    Fig. 16
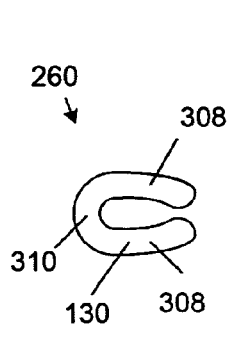 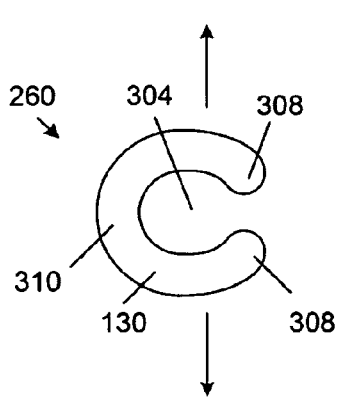 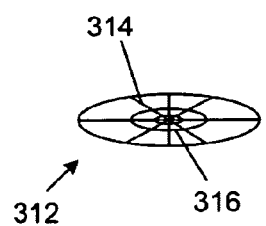
Fig. 17    Fig. 18    Fig. 19

SYSTEMS AND METHODS FOR VOLUME REDUCTION

CROSS-REFERENCE TO RELATED APPLICATION

This application is a continuation of International PCT Application No. PCT/US2007/061679 filed Feb. 6, 2007 which claims the benefit of U.S. Provisional Application No. 60/765,158, filed Feb. 6, 2006, which are both incorporated herein by reference in their entireties.

BACKGROUND OF THE INVENTION

This invention relates to systems and methods for reducing the volume of the left or right ventricles of the heart, thereby to facilitate treatment of congestive heart failure, ventricular aneurysms or other related conditions.

A spectrum of disease processes may affect the pumping capability of the heart, impairing its ability to provide adequate circulation for the metabolic needs of the tissues and organs of the body. Diseases specific to the heart include those that 1) interfere with the electrophysiological conduction to the heart; 2) interfere with the inflow or outflow of blood through a heart valve; or 3) affect the myocardium itself, whether by ischemic damage or intrinsic cardiomyopathy. Certain conditions may be improved by medical or surgical interventions, so that the heart is able to pump what the body requires. A conduction problem can be corrected, for example, by a pacemaker. An abnormal heart valve may be replaced.

Unfortunately, lesions of the cardiac muscle itself are more difficult, if not impossible, to repair at present. Techniques involving muscle regeneration by stem cells, for example, do not yet permit reliable restoration of functional myocardium. Instead, when the myocardium is injured, muscle cells that die are typically replaced with non-contractile scar tissue, and muscle cells that have been sublethally damaged may not contract normally. As a result, the heart may lose its ability to pump adequately. Impairment of the heart's contractile capability, if sufficiently severe or advanced, may result in diminished cardiac output (so-called forward failure), damming up of venous return (so-called backward failure), or both. These end results collectively form part of the syndrome of congestive heart failure (CHF).

Other CHF signs and symptoms are caused by the body's attempt to compensate for inadequate cardiac pumping. When the heart is not pumping enough blood to meet the body's demands, the body activates a number of compensatory physiologic mechanisms. If these physiological mechanisms are ineffective to restore adequate circulation, or if they become overextended, they no longer permit compensation. Instead, the system decompensates and may tip over into CHF.

Understanding the pathophysiology of CHF therefore involves understanding the compensatory mechanisms by which the heart responds to a mismatch between the body's metabolic needs and the heart's pumping capabilities. These compensatory mechanisms include: 1) the Frank-Starling mechanism, by which preload is increased to enhance cardiac performance; 2) myocardial hypertrophy, with an increase of contractile cell mass; 3) cardiac chamber dilation; and 4) neurohumoral adaptation, including the activation of the renin-angiotensin-aldosterone system and the release of norepinephrine. Under normal circumstances, these mechanisms work together to meet increased circulatory demands during exercise, stress or fever. When the demand on these adaptive mechanisms is too great, perhaps because of excessive metabolic requirements or inadequate pumping capability, the adaptive mechanisms themselves become maladaptive.

Under normal conditions, the heart responds to increasing demands by augmenting preload, increasing the heart rate, and increasing the contractility of the ventricles. An increase in preload leads to an increased stretch of the myocardial fibers. As a result, the force of the next cardiac contraction is increased, as described by the Frank-Starling curve. According to the Frank-Starling mechanism, the more the heart fills during diastole, the greater the force of contraction during the next systole. With overfilling of the heart, however, the cardiac muscle fibers become overstretched and this mechanism becomes ineffective. After a certain degree of stretch, the fibers no longer respond to increasing stretch by increasing contractility. Instead, their contractility diminishes. The overstretched heart becomes less able to pump, and the ventricles may dilate.

Over a longer period of time, cardiac muscle responds to increasing work demands by increasing in size, just like skeletal muscle. The cardiac muscle cells cannot increase in number, but can only increase in size. This mechanism is called hypertrophy. With myocardial hypertrophy, the ventricular wall thickness may increase and the ventricle may enlarge as the myocardial fibers elongate. The myocardial cell proteins formed during hypertrophy may be abnormal, however, which may affect their functional efficacy. Hypertrophy may also increase the myocardium's metabolic demands, such that these demands outstrip the circulatory supply.

Other cardiac compensatory mechanisms, such as increases in heart rate and contractility that are brought about by norepinephrine stimulation may exacerbate functional decompensation of the heart, because the metabolic needs of the cardiac muscle may increase beyond the circulation's ability to satisfy them. In addition, non-cardiac compensatory mechanisms set in motion by decreased cardiac output or contractility may also have adverse effects on myocardial function. For example, as the body compensates for decreased cardiac output by retaining sodium and water, there may be increased ventricular distention and a subsequent decrease in contractile efficiency. The body may respond by an additional increase in heart rate, increasing the myocardium's metabolic demands even further.

Where the compensatory mechanisms have lost their ability to improve cardiac performance appropriately or when the patient shows symptoms derived from the compensatory mechanisms or the underlying cardiac performance problem, medical intervention is warranted. Pharmacological treatment for CHF generally endeavors to increase myocardial contractility or to affect the now-dysfunctional compensation mechanisms. Three general classes of drugs have been found useful: 1) inotropic agents, which increase the strength of cardiac muscle contraction; 2) vasodilators, which decrease the resistance and head of pressure against which the heart must pump; and 3) diuretic agents, which counteract fluid retention and preload.

The New York Heart Association has proposed a useful functional classification system for CHF. Class I patients are not limited by cardiac symptoms and may engage in normal physical activity. Class II patients suffer symptoms like fatigue or dyspnea during ordinary physical activity. Class III patients experience a significant limitation of normal physical activities. Class IV patients suffer symptoms at rest or with any physical exertion. Pharmacological intervention may improve a patient's cardiac status sufficiently so that the person may enjoy an acceptable quality of life.

CHF, however, is accompanied by a grim prognosis. CHF patients may require multiple hospital admissions for management, and may deteriorate despite aggressive medical management. The majority of CHF patients may die within several years of diagnosis. NYHA Class IV patients may experience a 65% one-year mortality.

Heart transplantation has assumed a central role in the treatment of advanced CHF in certain patients. Transplantation, however, is a limited option, because of the restricted supply of donor organs and the need for immunosuppression. Nearly 5 million patients in the U.S. suffer from CHF. Approximately 500,000 patients are newly diagnosed each year. Yet fewer than 3,000 heart transplants are performed for this condition annually in the U.S., well below the number required to treat severely afflicted patients.

Standard surgical procedures such as coronary revascularization and mitral valve replacement are understood to be beneficial for certain CHF patients. Reconstruction of the mitral subvalvular apparatus may also improve left ventricular function in CHF patients. Implantable ventricular assist devices may provide temporary cardiac output support for CHF patients. A variety of surgical techniques permit reconstruction of the left ventricle itself, for example to treat a dyskinetic aneurysm or an akinetic segment following infarction. Partial left ventriculectomy may also involve excising viable but hypocontractile myocardium, to permit remodeling of the overstretched left ventricle. Dynamic cardiomyoplasty uses the patient's own skeletal muscle (e.g., the latissimus dorsi) to assist the heart in pumping and/or to decrease the stress on the myocardial wall. Passive ventricular constraint devices have been developed to improve cardiac function. For example, the Acorn CorCap™ offers flexible external constraint. In addition, devices may be positioned within the heart to constrain the size and/or shape of the ventricle.

There remains a need in the art for a treatment modality for CHF that helps to improve the anatomy and physiology of the failing left ventricle. A need also exists for a CHF treatment device that is adjustable once applied to the left ventricle, so that it can more closely adapt to the anatomic and physiological needs of the patient. Furthermore, there is a need for a device that is implantable using minimally invasive or catheter-based techniques in severely compromised CHF patients.

SUMMARY OF THE INVENTION

Provided herein are systems and methods for ventricular volume reduction.

A ventricular chamber volume reduction system disclosed herein comprises a containment system deliverable through an intravascular catheter into a ventricular chamber and expandable from a collapsed shape to a filled shape once delivered into the ventricular chamber; and a filler within the containment system, for example a resilient or non-resilient shell wherein the filler expands the containment system from the collapsed shape to the filled shape, and wherein the filled shape reduces volume of the ventricular chamber. The system reduces the chamber volume in a ventricular chamber, thereby reducing the effective volume of the ventricle. The term "effective volume" refers to the volume of blood that is ejected from the ventricle during systole or the volume of blood that is retained in the ventricle during diastole. The containment system may comprise an elastomeric component. The filler may be curable. The filler may comprise a polymer, which may be hydrophilic. The filler may be delivered by a catheter. The filler may reside within the containment system when the containment system is in the collapsed shape. The containment system may retain itself within the ventricular chamber. The retainment mechanism may be a self-expanding support or frame. The system may further comprise attachment mechanisms that affix the containment system to a wall of the ventricular chamber.

The system may further comprise a fillport for the containment system. The fillport may be adapted for delivery of additional filler to the containment system when the containment system is positioned within the ventricular chamber. The fillport may be adapted for removal of filler from the containment system when the containment system is positioned within the ventricular chamber. The fillport may be adapted for delivery of a fluid into the containment system when the containment system is positioned within the ventricular chamber. The fillport may be adapted for removal of fluid from the containment system when the containment system is positioned within the ventricular chamber.

A ventricular chamber volume reduction system disclosed herein can comprise a container body deliverable into a ventricular chamber and expandable from a first shape to a second shape when delivered into the ventricular chamber, the container body having a tissue surface in contact with a wall of the ventricular chamber and an exposed surface facing into the ventricular chamber, wherein the second shape of the container body occupies space in the ventricular chamber, thereby reducing ventricular volume. The system reduces the chamber volume in a ventricular chamber, thereby reducing the effective volume of the ventricle. The container body comprises a reinforcement framework dimensionally adapted for supporting the second shape of the container body. The first shape of the container body is dimensionally adapted for delivery through a catheter. The container body comprises an attachment device that affixes the tissue surface to the wall of the ventricular chamber.

A ventricular chamber volume reduction system disclosed herein can comprise a partition sequestering a portion of a ventricular chamber, thereby removing the portion from a flow path for blood flowing within the ventricular chamber, the partition having an exposed surface facing the flow path and a support to secure its position within the ventricular chamber, wherein placement of the partition decreases volume of blood flowing along the flow path within the ventricular chamber. The partition may reduce the volume of blood ejected during systole or the amount of blood retained during diastole. The system reduces the chamber volume in a ventricular chamber, thereby reducing the effective volume of the ventricle. The partition may further comprise an antithrombotic agent and/or other medicaments.

The system may further comprise a support intrinsic to the partition. The support may be affixed to the wall of the ventricular chamber. The support may further comprise a plurality of ribs reinforcing the partition. The system may further comprise a framework affixed to the partition. The framework may further comprise a tether attaching the partition to a wall of the ventricular chamber. The framework may apply a contractile force to the wall of the ventricular chamber. The framework may comprise an elastomeric material.

The system may further comprise an anchor to attach the partition directly to the wall of the ventricular chamber. In embodiments, the system may further comprise a filler occupying the portion of the ventricular chamber sequestered by the partition. The system may further comprise a solid body occupying the portion of the ventricular chamber sequestered by the partition. A solid body may include any solid structure dimensionally adapted for occupying space within the partitioned portion of the ventricular chamber. The system may further comprise an expandable body occupying the portion of the ventricular chamber sequestered by the partition.

Methods for reducing ventricular volume disclosed herein can comprise delivering a containment system into a ventricular chamber and expanding the containment system from a collapsed shape to a filled shape within the ventricular chamber, thereby reducing ventricular volume. The filled shape of the containment system may be affixed within the ventricular chamber.

Methods for reducing ventricular volume disclosed herein can comprise delivering a container body into a ventricular chamber, and expanding the container body from a first shape to a second shape, wherein the second shape occupies space in the ventricular chamber, thereby reducing ventricular volume. The container body may be affixed within the ventricular chamber.

Methods for reducing effective ventricular volume disclosed herein can comprise partitioning a ventricular chamber into a flow path and a no-flow path, thereby reducing effective ventricular chamber volume. A flow path is understood to be a volume of the ventricle through which circulating blood flows. A no-flow path is understood to be a volume of the ventricle that is sequestered from the flow path, so that it is not accessible to circulating blood.

BRIEF DESCRIPTION OF FIGURES

The systems and methods described herein may be, understood by reference to the following figures:

FIG. 14 illustrates a variation of the volume reduction system.

FIGS. 15 and 16 illustrate variations of the volume reduction system.

FIGS. 17 and 18 illustrate a top view of the variation of the volume reduction system of FIG. 15 in deflated and inflated configurations, respectively, not to scale.

FIG. 19 illustrates a variation of a cover.

DETAILED DESCRIPTION OF FIGURES

Figure 1:
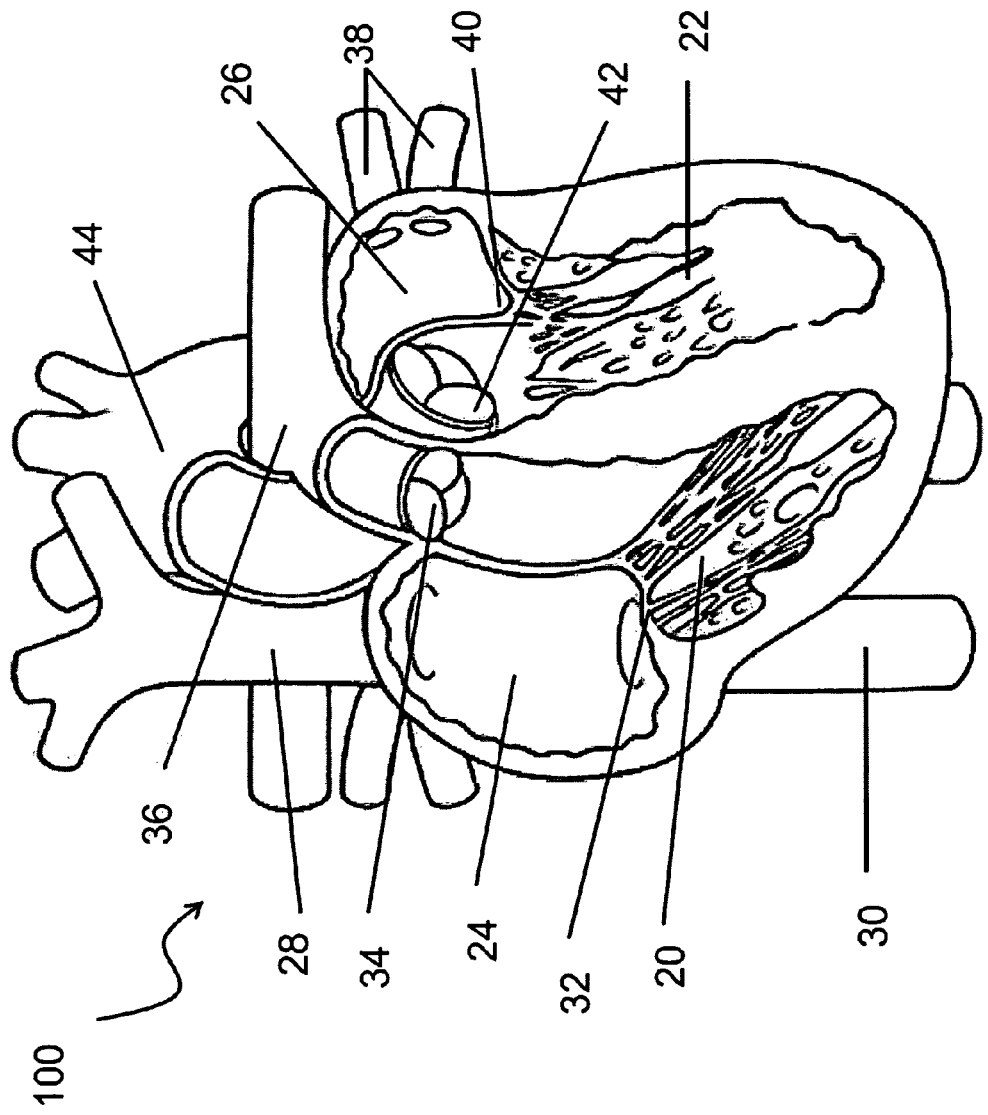
FIG. 1 shows a partial cut-away view of a human heart

FIG. 1 illustrates the structures of the human heart 100. In more detail, a right ventricle 20 and a left ventricle 22 are shown. Blood returning from the systemic circulation passes into the heart 100 through the superior vena cava 28 and the inferior vena cava 30, thereafter entering the right atrium 24 of the heart 100. The deoxygenated blood passes from the right atrium 24 through the tricuspid valve 32 into the right ventricle 20. The right ventricle 20 pumps the blood through the pulmonic valve 34 into the pulmonary artery 36, which conducts the deoxygenated blood into the lungs. Oxygenated blood returns to the heart 100 through the pulmonary veins 38. The blood then enters the left atrium 26 and passes through the mitral valve 40 into the left ventricle 22. The left ventricle 22 pumps the oxygenated blood through the aortic valve 42 into the aorta 44 for distribution into the systemic circulation.

Figures 2A, 2B:
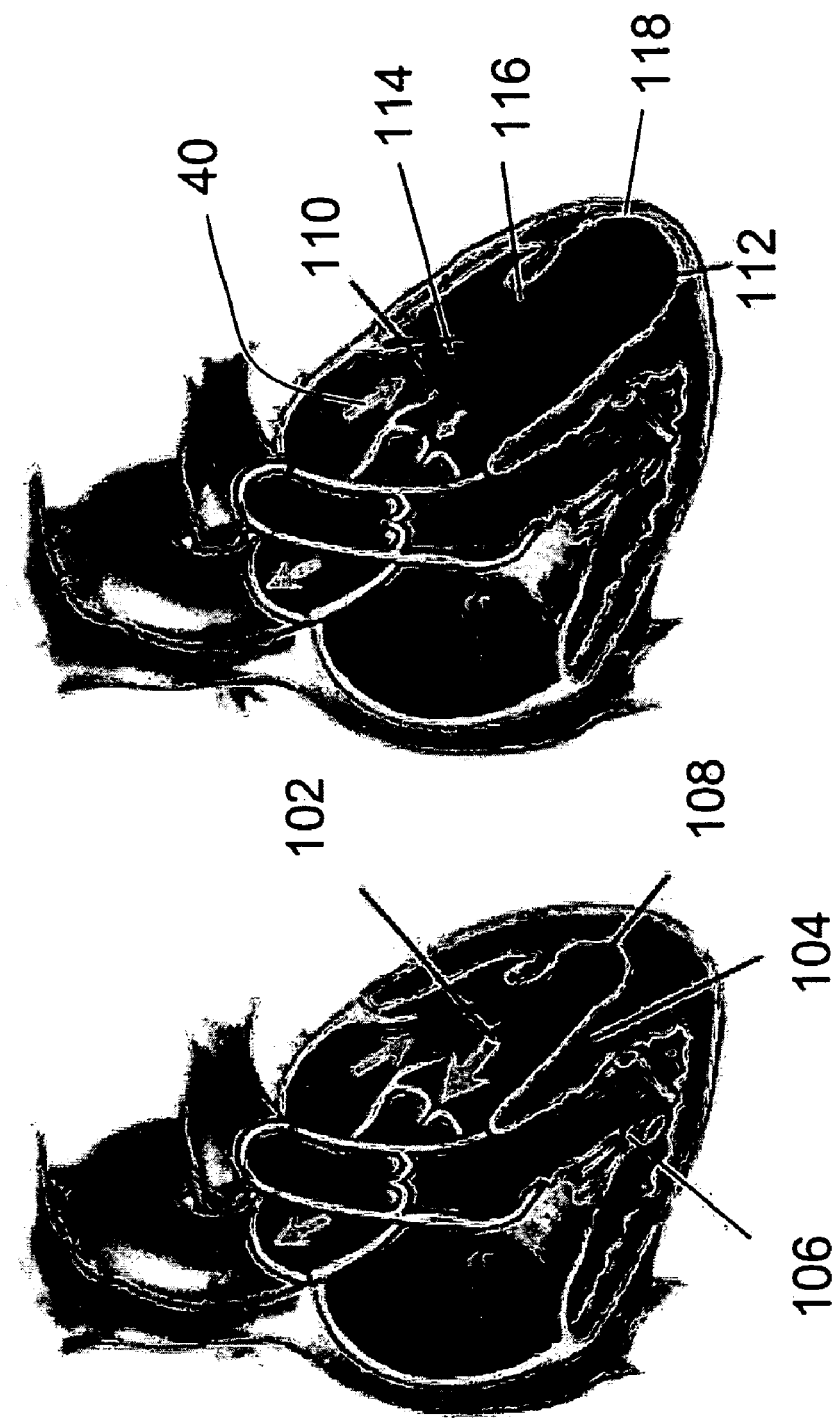
FIGS. 2a and 2b partial cut-away views of a human heart illustrating, respectively, normal anatomy and certain anatomic changes accompanying congestive heart failure.

FIG. 2a schematically illustrates normal cardiac anatomy. The right ventricle 106 and the left ventricle 108 are normally sized and shaped. Arrows in the diagram represent the path of blood flow through the left side of the heart. The arrow 102 is sized to represent a normal cardiac output, consistent with the normal physiology shown in FIG. 2a. In a normal heart, the ejection fraction (the volume of blood ejected divided by the total ventricular volume) is typically greater than 60%.

FIG. 2b schematically illustrates certain changes in cardiac anatomy and physiology under conditions of congestive heart failure (CHF). The arrow 110 is sized to represent a decreased cardiac output, consistent with the hemodynamics of CHF. In severe CHF, cardiac output may be decreased and end-diastolic ventricular volume may be increased. The ejection fraction may be as low as 20-30%. As depicted in FIG. 2b, the left ventricle 112 is dilated and the ventricular wall 118 is thinned. The position of one of the chordae tendinae 114 and papillary muscles 116 is also schematically depicted. With dilation of the ventricle 112, the relative positions of these structures may be altered, affecting their ability to tether the mitral valve 40 during ventricular contraction. With severe CHF, the alteration of mitral valve 40 geometry or of the tethering apparatus may result in mitral valve 40 regurgitation.

The systems and methods in this specification are described with reference to the generalized anatomy and physiology of congestive heart failure as depicted in FIG. 2b. Decreasing the left ventricular volume in CHF may improve the ejection fraction and may stabilize or improve CHF symptoms. The systems and methods described below may act as static space occupying structures that passively decrease ventricular volume. These systems and methods may further have dynamic properties, acting to pull the myocardial walls inward for example, thereby further decreasing ventricular volume.

The systems and methods described below would be applicable to other anatomic conditions, including ventricular aneurysms and dyskinetic ventricular segments. Adaptations of the systems and methods disclosed herein may be provided to address such conditions, requiring no more than routine experimentation. The systems and methods disclosed herein may be adapted for treatment of related anatomic abnormalities such as mitral regurgitation, dilation of the mitral valve annulus and the like. The systems and methods described herein may be combined with any other active or passive system to exert a static or dynamic force on the left ventricular wall, the anatomic components of the ventricular wall, the mitral valve or its supporting structures.

Figure 3:
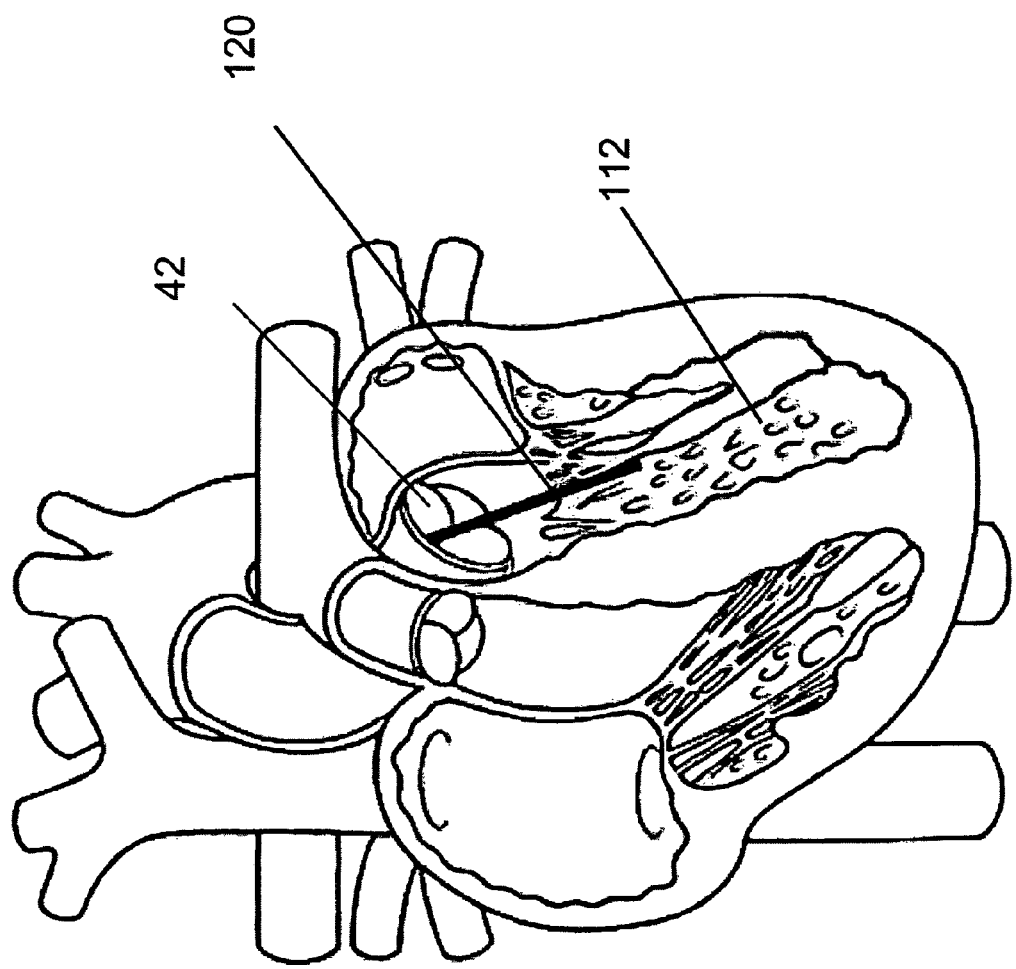
FIG. 3 shows a partial cut-away view of a human heart illustrating the transaortic placement of a delivery catheter.

As depicted in FIG. 3, a system constructed in accordance with the principles of the present invention may permit the delivery of an expandable device into the dilated left ventricle 112 of a patient with CHF. To enter the left ventricle 112, a catheter-type delivery device 120 may be used. As would be understood by those of ordinary skill in the art, such a delivery device 120 could be inserted into the ventricle retrograde through the arterial system, crossing the aortic valve 42. Other placement routes can be used. For example, the delivery catheter 120 could be passed transvenously into the right atrium and then directed across the intraatrial septum via puncture to enter the left atrium, crossing the mitral valve to enter the left ventricle 112. While minimally invasive delivery is desirable, using for example a catheter-type delivery device 120, other delivery methods may also be envisioned. For example, a thoracoscopic technique may be used, or an open surgical technique. In addition, the volume reduction device described herein may be delivered as an adjunct to another procedure, for example a coronary artery bypass or a valve replacement. Other placement methods may be envisioned by those of ordinary skill.

Figure 4:
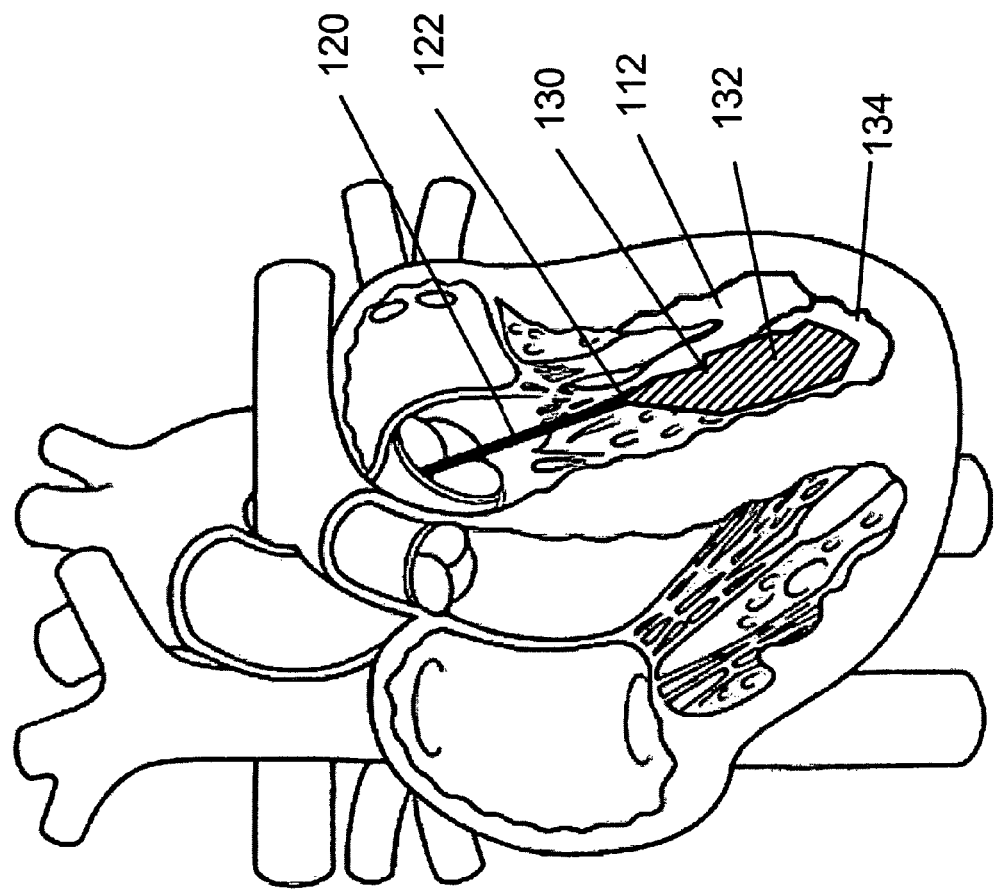
FIG. 4 shows a partial cut-away view of a human heart illustrating the placement of a volume reduction device via a delivery catheter.

FIG. 4 illustrates steps of the delivery of a volume reduction system into the left ventricle 112. As depicted in this figure, a volume reduction system may comprise one or more containment systems 130, for example a fluid and/or gel and/or solid containment element or system. The containment systems 130 can be filled with one or more filler materials 132. The catheter 120 may maneuver into position within the left ventricle 112. The catheter 120 may deliver the volume reduction device containment system 130 into the ventricle 112. The containment system 130 may be inserted into the ventricle in a first, collapsed shape. The catheter 120 may be used to position the containment system 130 so that the containment system 130 seats properly in the ventricle 112, for example against the ventricular wall 134. Practitioners of ordinary skill may be able to determine how best to position the containment system 130 in the ventricle 112, avoiding, for example, interference with the functioning of the papillary muscles (as depicted in FIG. 2b), or avoiding impingement upon the chordae tendinae (as depicted in FIG. 2b).

A containment system 130 may be made of any biocompatible material that suitably contains the filler material 132. The containment system 130 can be formed from an elastomeric material. The elastomeric material can permit the filled containment system 130 to flex in response to ventricular contractions. The containment system 130 may be formed from several different materials, or from materials whose stress-strain characteristics permit differential stiffness and/or flexing in one direction preferentially. The containment system 130 may be formed from ePTFE, PTFE, from silicone, or from other polymers, as would be understood by those of ordinary skill in the art.

After the delivery of the containment system 130 into the ventricle 112, or simultaneous with extrusion of the containment system 130 from the catheter 120, a filler material 132 may be delivered into the containment system 130. The containment system may have independent compartments that may be filled independently to varying pressure or may be filled with different materials. Insertion of the filler material 132 may expand the containment system to a second, filled shape. The catheter 120 may be used to position the containment system 130 within the ventricle 112 as it is being filled or after it has been filled. The containment system 130 may be prefilled with a hydrophilic filler that absorbs water and thus expands to a filled shape. The catheter 120 may be used to apply force to the filled containment system 130 to attach it to the ventricle wall 134. The catheter 120 may also provide mechanisms for activating ancillary structures that form part of the volume reduction system, as will be described in more detail below.

As shown in this figure, a filling port 122 may be placed in the proximal end of the containment system 130 through which filler material 132 enters the containment system. A filling port 122 may be self-sealing, so that it seals permanently when the catheter is detached from the containment system 130. The filling port 122 may permit repeated access, so that the volume of filler material 132 may be adjusted by subsequent catheterizations. A suitable filling port 122 permitting repeated access by subsequent catheterization may have a screw mechanism, a latch mechanism, or any other mechanism that would permit detachable attachment of a filling device. The filling port 122 may include a valve (not shown), such as a flap valve or ball valve. A two-way valve structure may permit both filling and emptying of the filler material 132. The filling port 122 may also be accessible by a needle to add or remove filler material 132. Adjustability of filling volume may permit the physician to increase or to decrease the space within the ventricle 112 occupied by the volume reduction system.

The containment system 130 may be overfilled using a first filler material 132a (not shown). The first filler material 132a may be removed and replaced by a smaller volume of a second filler material 132b (not shown). Alternatively, a portion of the first filler material 132 may be removed to adjust the volume as desired. The initial process of overexpansion may enhance the seating of the filled containment system 130 within the ventricle 112.

Appropriate filler material 132 may include biocompatible gases or liquids. The filler material 132 may be a saline solution or any other biocompatible solution, including polymeric materials, polyethylene glycols, collagen solutions, fibrin solutions, water, blood, gas (e.g., carbon dioxide, air, oxygen, nitrogen, nitrous oxide), and combinations thereof. The filler material 132 may be curable or may otherwise change its viscosity and physical properties before or after filling. The filler material 132 is cured or hardened to provide for a permanent implant having, for example, a fixed size and shape conforming to the anatomy of the ventricle 112. Methods for curing or hardening the filler material 132 are specific for particular filler materials 132. For example, certain polymers may be cured by exposure to ultraviolet light or to heat, including body heat. Other curing systems may be set up by mixing two polymers together. In such a case, the catheter 120 may permit delivery of the two component polymers, so that their mixing inside the containment system 130 will result in a single cured filler material 132. Certain polymers may be mixed immediately before use, and then inserted through the catheter 120 into the containment system 130, with the expectation that they will cure within the containment system 130 within a predetermined time. Curing need not result in a firm filler material 132. Elastomers, gels, sols, foams and other liquid, semisolid or solid filler materials 132 and the like having a range of consistencies from soft to firm, may be suitable for these purposes. Radiopaque marker materials may be used as filler materials 132 or may be added to filler materials 132.

The filler material 132 may possess contractile properties, or may contract when cured so that it urges the volume reduction system to decrease its volume. If the containment system 130 of the volume reduction system has been affixed firmly to the ventricular wall 134, contraction of the filler material 132 may exert an inward pull on the ventricular wall 134, thereby further reducing ventricular volume.

Figure 5:
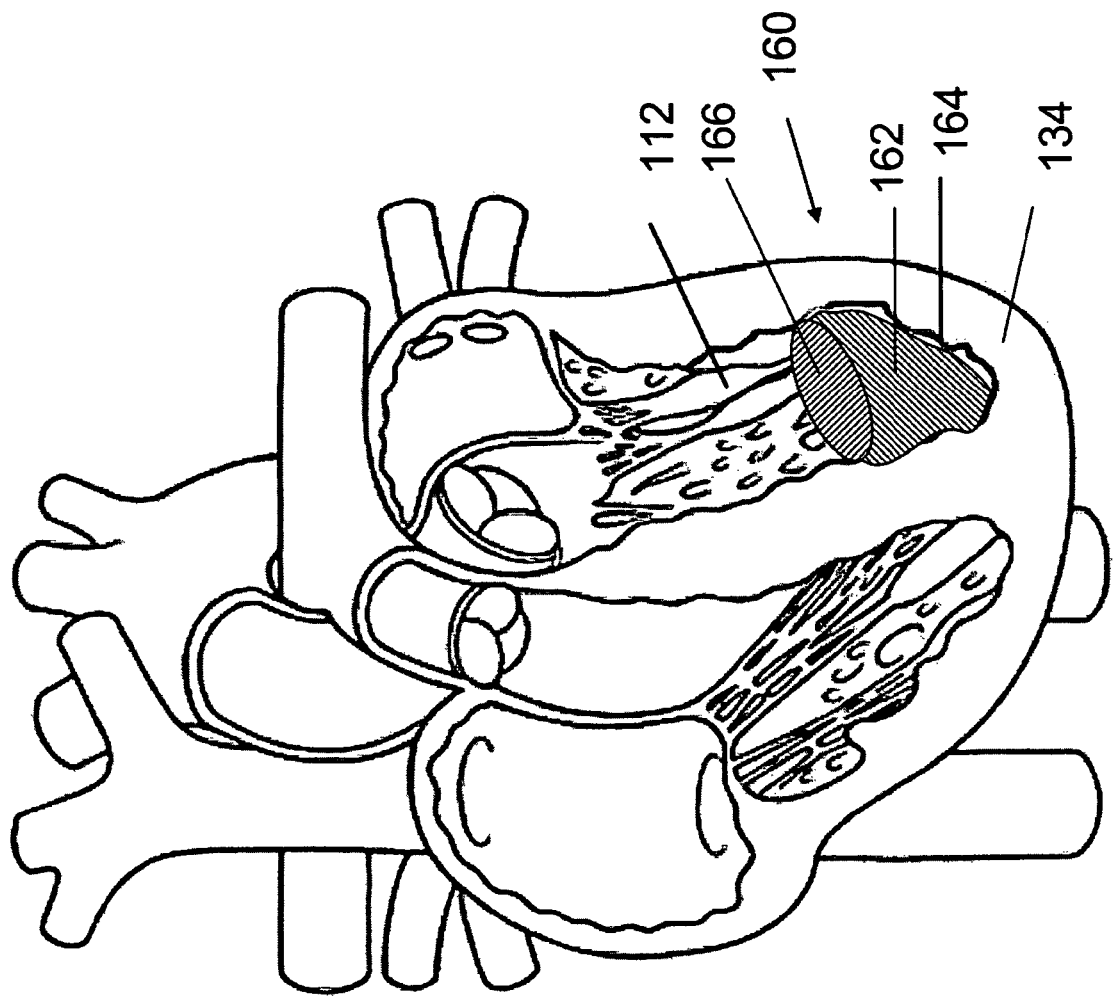
FIG. 5 illustrates a variation of a volume reduction device.

FIG. 5 depicts a volume reduction system 160 seated within the left ventricle 112. As shown in this figure, a volume reduction system 160 may include a volume reduction container body 162 that contains filler material as described above. The container body 162 can have a tissue surface 164 that abuts the ventricular wall 134, and has an exposed surface 166 that is in contact with free-flowing blood in the cavity of the left ventricle 112.

The container body 162 can abut against the ventricular wall 134 and may substantially conform to its shape. The solidifying of the filler material (not shown) may enhance the conformity of the container body 162 to the irregularities of the ventricular wall 134. Conformity of the container body 162 to the wall can facilitate its retention in the ventricle 112. The tissue surface 164 of the container body 162 may be modified to enhance attachment, for example by facilitating endothelialization or other physiological anchorage. For example, the tissue surface 164 may be textured, or may be covered with a fabric or mesh that would provide a template for tissue ingrowth. Any surfaces of the container body 162 may bear radioopaque markers, may contain radioopaque filler material, or may otherwise be radioopaque.

The exposed surface 166 may be part of the same assembly as the container body 162. For example, a balloon-like container body 162 may assume a spherical or ovoid shape that nestles distally in the apex of the ventricle 112, and that protrudes convexly into the chamber of the ventricle 112. The superior aspect of the container body 162 protruding into the ventricle 112 can itself form the exposed surface 166.

Such as depicted in FIG. 5, the exposed surface 166 may assume its own geometry, apart from the shape assumed by the container body 162. As shown in FIG. 5, a two-part assembly with a container body 162 element and an exposed surface 166 element can be joined together. The container body 162 and the exposed surface 166 may be made from different materials, each having different physical properties. For example, the container body 162 may be made from a highly elastic material that allows it readily to conform to the interior configurations of the ventricle 112, while the exposed surface 166 may be a stiffer material that is inclined to assume a predetermined shape. The container body 162 may be an integral assembly with the exposed surface 166 but the geometry of the unit may be determined in part by the materials from which each aspect is formed, or may be determined in part by any framework or support included within the substance of the unit.

It is understood that the exposed surface 166 will be in contact with free-flowing blood. Therefore, anti-thrombotic materials are desirable for the exposed surface 166, as is a shape that avoids areas of stasis. Resistance to thrombosis may be inherent in the selected material forming the exposed surface 166, or it may be produced by applying a suitable coating to or embedding a suitable antithrombotic material in the biomaterial comprising the exposed surface 166.

Reinforcement materials may be embedded in or integrated into the components of the volume reduction system. Such reinforcement materials may include struts or stents included in the container body 162 or the exposed surface 166. The reinforcement materials may cause the component to assume a predetermined shape. For example, there may be a hoop (not shown) made from a polymer, a flexible metal or a shape memory material that is imbedded in the periphery of the exposed surface 166. The hoop or similar structure may direct the exposed surface 166 to assume the predetermined shape, for example, an oval or a circle. As another example, there may be ribs (not shown) based centrally within the substance of the exposed surface 166 and spreading out radially. The ribs or similar structures may direct the exposed surface 166 to assume the predetermined shape. Reinforcement materials may also provide for structural strength or stability in the container body 162, the exposed surface 166 or both. For example, a net of fine metallic fibers (not shown) surrounding the container body 162 may be provided to reinforce the container body 162 and/or to offer protection for example against material fatigue that may result from repeated flexion in response to ventricular contraction and relaxation.

Figure 6:
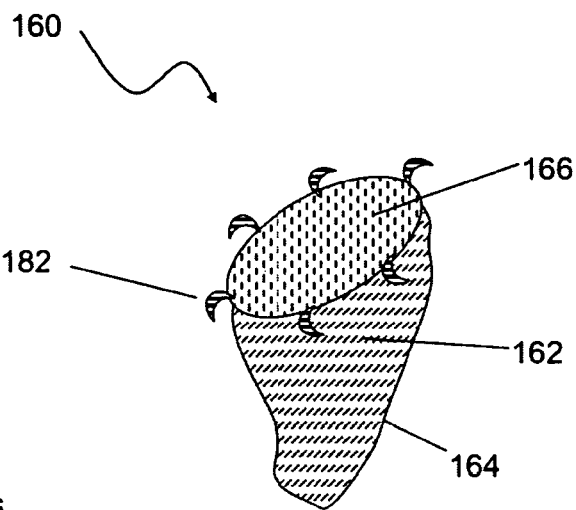
FIG. 6 shows a partial cut-away view of a human heart illustrating a variation of a volume reduction device positioned in the left ventricle.

FIG. 6 depicts a volume reduction system 160 that can have a container body 162, a tissue surface 164 and an exposed surface 166. Situated around the periphery of the exposed surface 166 and integral therewith are a plurality of attachment devices 182 that may attach the volume reduction system 160 to the wall of the ventricle. As depicted, there are six attachment devices 182 shaped like hooks or claws. Attachment devices may take a variety of shapes, including barbs, prongs, fishhooks, claws, spikes or any other shape that would attach the system 160 to the surrounding tissues. The attachment devices 182 may be detachable, so that the system 160 may be removed in its entirety. The attachment devices 182 may be biodegradable, or may provide only temporary attachment. The attachment devices 182 may be of any size or number that provides satisfactory attachment. There may be a single attachment device 182 or a plurality of attachment devices 182. For example, a large number of tiny attachment thistle-like fibers may provide adequate attachment. Or, for example, nanomaterials may be available to provide attachment. Attachment devices 182 may be positioned anywhere upon the volume reduction system 160, and need not be confined to the periphery of the exposed surface 166. For example, a plurality of small upwardly-directed barbs may be embedded in the tissue surface 164 of the container body 162 providing attachment over a large area and resisting displacement. As another example, the container body 162 may be surrounded by a very fine polymeric or metallic net having attachment devices 182 integrated therewith.

Figure 7:
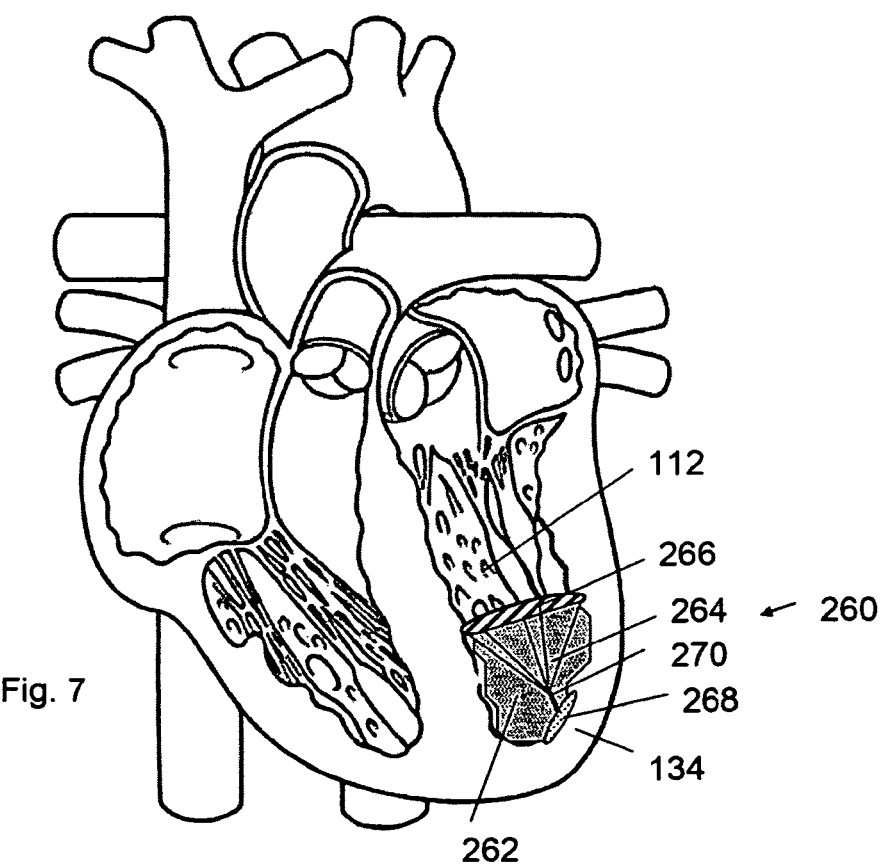
FIG. 7 shows a partial cut-away view of a human heart illustrating a variation of a volume reduction device positioned in the left ventricle.

FIG. 7 depicts a volume reduction system 260 positioned within the left ventricle 112 and partitioning off from the left ventricle an interior volume 262 that is separated from the free flow of blood within the ventricle. The path where blood flows freely within the ventricle may be termed the flow path for blood. The depicted volume reduction system 260 includes an exposed surface 266 attached to and supported by a framework 264. The exposed surface 266 may be shaped as a lid or a cap sealing off an interior volume 262. The framework 264 passes through the internal volume 262 to terminate in an anchoring foot 268 that attaches the framework 264 to the ventricular wall 134.

The exposed surface 266 may be made from any biocompatible material, for example an antithrombotic material. The exposed surface 266 can be in contact with free-flowing blood. The exposed surface 266 can be made from anti-thrombotic materials. The exposed surface 266 can be formed into a shape that avoids areas of stasis. Resistance to thrombosis may be inherent in the selected material, or it may be produced by applying a suitable coating to or embedding a suitable antithrombotic material in the biomaterial comprising the exposed surface 266. The exposed surface 266 may have a sufficient degree of elasticity that it can respond without fatigue to stresses from ventricular contraction and relaxation. The exposed surface 266 may bear attachment devices (not shown) around its periphery to secure it in a preselected position within the ventricle 112. The exposed surface 266 may incorporate a band around its periphery to permit tissue ingrowth for anchoring.

The exposed surface 266 may be a solid material having its own thickness and volume. The exposed surface 266 may have a support (not shown) embedded within it. The exposed surface 266 may be made of a lightweight material supported by its internal support (not shown). The geometry of the exposed surface 266 may be adapted to the shape of the interior of the ventricle 112. The exposed surface 266 may be flat, convex or concave.

The framework 264 supports the exposed surface 266 and attaches it to the anchoring foot 269. The framework 264 desirably has elastic properties that permit it to respond to ventricular contraction and relaxation without fatigue and without erosion into surrounding tissues. Suitable materials for the framework 264 may include polymers, metals, shape memory materials and the like. The framework 264 depicted in FIG. 6 is comprised of ribs attached to a central tether 270. The central tether 270 is in turn attached to the anchoring foot 268. The ribs may spring out from the central tether and exert a radial force against the periphery of the exposed surface 266, thereby holding the exposed surface 266 open and supporting it against the contraction and relaxation of the ventricle 112. Other configurations for the framework 264 may be apparent to practitioners of ordinary skill. For example, the framework 264 may include a spring or a coil that assumes a predetermined shape upon release from a delivery catheter (not shown), or that forms into a predetermined shape upon exposure to body temperature as a shape memory material.

The framework 264 is affixed to an anchoring foot 268 that attaches the entire system 260 to the ventricular wall 134. As depicted in FIG. 7, the framework 264 attaches to a central tether 270 which in turn attaches to the anchoring foot 268. It is understood that any type of attachment between the framework 264 and the anchoring foot 268 may be envisioned.

The anchoring foot 268 permits attachment of the framework 264 to the ventricular wall 134. The anchoring foot 268 may include barbs, hooks, anchors, claws, fasteners, screws, and the like, that allow affixation to the tissue. Configurations of the anchoring foot 268 may vary depending on the thickness of the ventricular wall 134 and/or the health of ventricular wall 134 tissues. For example, an anchoring foot 268 may need a broad base without much penetrating depth in patients with thinned ventricular wall tissues. Or, for example, the anchoring foot 268 may be screwed into the tissues of the ventricular wall 134 if the tissues are of sufficient thickness and strength. Other variations of the anchoring foot 268 will be apparent to those of ordinary skill in the art.

An interior volume 262 exists beneath the exposed surface 266. This interior volume 262 may be filled with a filling material that occupies the volume and provides support for the entire system 260. The filling material may be placed within a containment bag (not shown) that occupies the interior volume 262. The filling material may be inserted without any other containment besides the cap on the interior volume 262 afforded by the exposed surface 266. Filling materials that occupy the interior volume 262 may be similar to those described above. Filling materials may be introduced into the interior volume 262 or into any containment bag therein through a fill tube, a fill port, a needle, or the like. Moreover, a solid body or an expandable body (not shown) may be placed within the interior volume 262 to occupy space therein.

The framework 264 may have contractile properties so that it exerts traction on the exposed surface 266 to decrease the size of the interior volume 262. This may allow the volume reduction system 260 to shape the ventricle over time to enhance ventricular function. Similarly, material introduced into the interior volume 262 may have contractile properties, so that it tends to reduce the size of the interior volume 262 and reshape the ventricle over time. A valve system may permit adjustment of interior volume by adding or removing filling material.

While the framework 264 shown in FIG. 6 is contained within the interior volume 262, a volume reduction system 260 may include a framework that surrounds or envelops the interior volume 262. For example, a framework 264 may be shaped as a coil arranged around the periphery of the interior volume 262 that supports the exposed surface 266. As another example, a framework 264 may be a balloon shaped as a coil or as a series of toroidal structures arranged around the periphery of the interior volume 262 and supporting the exposed surface 266. A balloon acting as a framework 264 may be filled with any of the sorts of filler materials previously described. The volume of a balloon framework 264 may be adjusted, for example by adding or removing filler material. Employing a balloon as a framework 264, filling the balloon may enhance the anchorage of the volume reduction system 260 within the ventricle 112. The toroidal structure or balloon system may act as solid or expandable bodies occupying space within the interior volume 262, and may not act as a framework or support.

Figure 8:
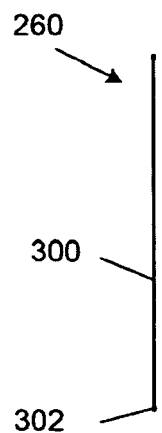
FIGS. 8 through 12 illustrate variations of the volume reduction system in various configurations.

FIG. 8 illustrates that the volume reduction system 260 can have a first configuration that is substantially straight. The first configuration of the volume reduction system 260 can be in a relaxed or a stressed and biased state. The volume reduction system 260 can have a rigid or flexible frame 300. The frame 300 can have one or more wires, rods, shafts, ribbons, or combinations thereof. The frame 300 can be hollow and/or solid. The volume reduction system 260 can have one or more atraumatic tips 302 at the proximal and/or distal ends of the volume reduction system 260. The atraumatic tips 302 can be rounded, bulbous, softened, or combinations thereof.

Figure 9:
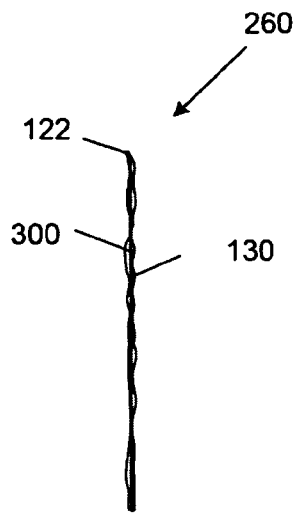

FIG. 9 illustrates that the volume reduction system 260 can have the containment system 130 on the frame 300. The containment system 300 can be in a deflated configuration. The containment system 130 can have one or more fill ports 122 at the proximal and/or distal ends of the containment system 130. The fill ports 122 can be self-sealing.

Figure 10:
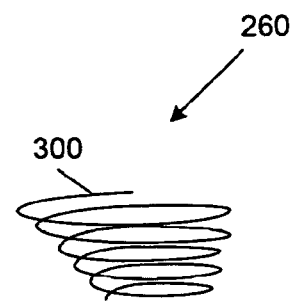

FIG. 10 illustrates that the frame 300 can have a helical or spiraled relaxed or biased configuration. The frame 300 can have a tapered configuration. For example, the frame 300 can have a taped helical or spiral configuration, such as a conical configuration. The frame 300 and/or inflated containment system 130 (as shown in FIG. 11) can have a configuration that can mimic the shape of the interior of a biological space, such as the apex of the left ventricle, a fallopian tube, or a stomach.

Figure 11:
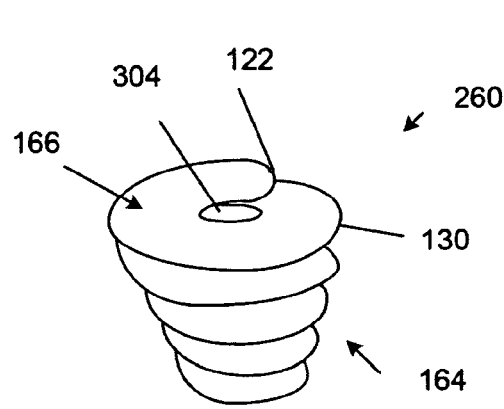

FIG. 11 illustrates that the containment system 130 a helical or spiraled configuration in a wholly or partially inflated or deflated configuration. The containment system 130 can have a tapered configuration in a wholly or partially inflated or deflated configuration. For example, the containment system 130 can have a taped helical or spiral configuration, such as a conical configuration in a wholly or partially inflated or deflated configuration.

The exposed surface 166 can have a central port 304. The central port 304 can be open into a central lumen and or be covered by a port cover.

Figure 12:
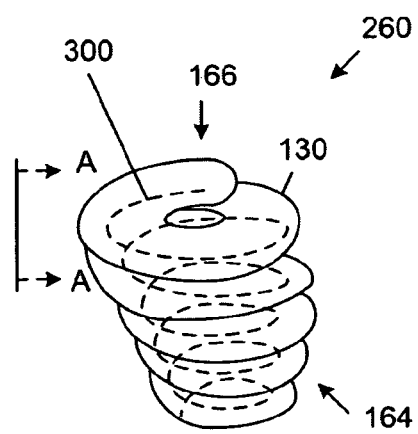

FIG. 12 illustrates that the frame 300 can be in the containment system 130 when the containment system is in an inflated or otherwise expanded configuration.

Figure 13A:
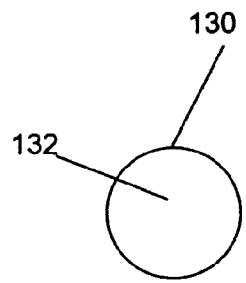
FIGS. 13a through 13f illustrate variations of cross-section A-A of FIG. 12.

FIG. 13a illustrates that the containment system 130 can be filled with the filler material 132. The containment system 130 can have no frame 300 and/or the frame 300 can be less than the length of the containment system 130.

Figure 13B:
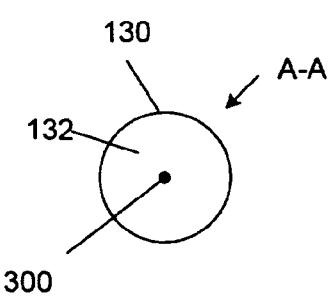

FIG. 13b illustrates that the frame 300 can be configured to be substantially radially central to the containment system 130, for example, when the containment system 130 is in a partially and/or fully inflated or otherwise expanded configuration. The frame 300 can have a hollow or solid circular transverse cross-section, as shown. The frame 300 can have a hollow or solid triangular, rectangular, oval, square, pentagonal, or I-beam transverse cross-section, or combinations thereof.

Figure 13C:
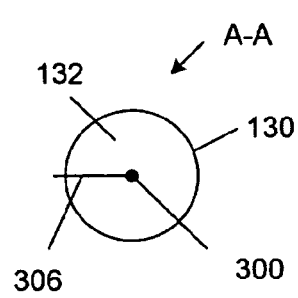

FIG. 13c illustrates that one or more barbs or rails 306 can extend radially from the frame 300. The frame 300 can be attached and/or integral with the bars or rails 206. The barbs and/or rails 306 can extend through the containment system 130 across a fluid-tight or a not fluid-tight seal.

Figure 13D:
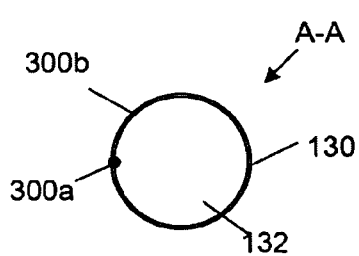

FIG. 13d illustrates that the frame 300 can have one or more frame spines 300a and one or more frame hoops 300b. The frame spine 300a can be integral with and/or directly attached to the containment system 130. The frame 300 can be an exoskeleton or exoframe on the outside of the containment system 130. The frame 300 can be resilient or deformable. The frame hoop 300b can radially expand as the containment system 130 is inflated or otherwise expanded. One or more barbs, rails, anchors, or combinations thereof, can extend radially from the hoop 300b.

Figure 13E:
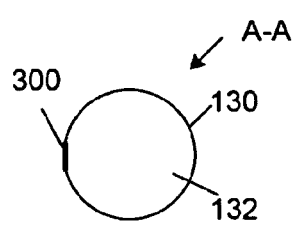

FIG. 13e illustrates that the frame 300 can have or be a ribbon. The ribbon can have a straight transverse cross section (as shown). The ribbon can be radially central with respect to the containment system 130 and/or radial offset with respect to the containment system 130, for example integral with and/or directly attached to the containment system 130.

Figure 13F:
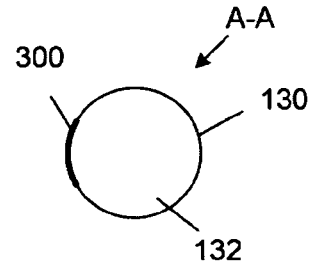

FIG. 13f illustrates that the frame 300 (e.g., the ribbon) can have a curved transverse cross-section, for example, matching the curvature of the containment system 130.

FIG. 14 illustrates that the volume reduction system 260 can have a substantially straight configuration in an inflated or otherwise expanded configuration. The volume reduction systems 260 can be deformed when deployed into biological spaces with anatomy non-conforming to the volume reduction system 260. For example, the volume reduction systems 260 shown in FIGS. 8, 9 and 14 can be positioned at a target site and then deformed (e.g., by a tool and/or by pressing against the tissue wall) to substantially fit the anatomical target site.

FIG. 15 illustrates that the volume reduction system 260 can have one or more containment system spines 310 extending longitudinally along a longitudinal axis of the volume reduction system 260. The volume reduction system 260 can have one or more sets of singular or opposing containment system fingers 308 extending from the containment system spine. The frame 300 (not shown) can have one or more frame spines and/or frame fingers.

FIG. 16 illustrates that the containment system fingers 308 at a distal end of the volume reduction system 260 can have a larger radii than the containment system fingers 308 at a proximal end of the volume reduction device 260. The containment system fingers 308 can taper along the length of the containment system spine 310.

FIG. 17 illustrates the volume reduction system 260 in a partially or completely deflated or otherwise contracted configuration. FIG. 18 illustrates the volume reduction system 260 in a partially or completely inflated or otherwise expanded configuration. When partially or completely deflated or contracted, opposing containment system fingers 308 can be substantially nearer each other than when more inflated or expanded. FIG. 18 illustrates that the opposing containment system fingers 308 can expand radially outward, as shown by arrows, when the containment system 130 is inflated or otherwise expanded. The containment system fingers 308 can frictionally fit against the surrounding anatomical surface.

FIG. 19 illustrates that a cover 312 can have radial filaments 314 and/or angular filaments 316. The cover 312 can have a metal, fabric or polymer substrate. The cover 312 can be rigid, deformable or elastic. The cover 312 can have an elasticity to provide a harmonic spring-like effect to increase systolic pumping force when located in the ventricle. The containment system 130 and/or frame 300 can have an elasticity to provide a harmonic spring-like effect to increase systolic pumping force when located in the ventricle. The cover 312 can be attached to and/or integral with the central port 304. The cover 312 can be sized to cover the central port 304 and/or the exposed surface 166.

Figure 20:
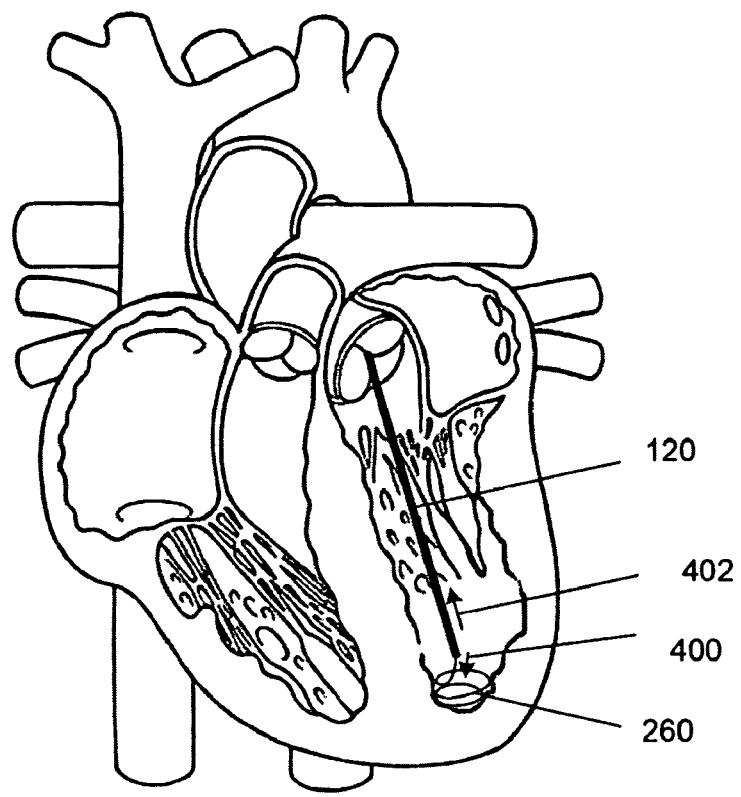
FIGS. 20 and 21 illustrate a variation of a method for deploying a variation of the volume reduction system in the left ventricle.

FIG. 20 illustrates that the volume reduction system 260 can be deployed into the left ventricle by a catheter 120. As the volume reduction system 260 can be stressed into a substantially straight configuration in the catheter 120. As shown by arrow 400, as the volume reduction system 260 exits the catheter 120, the volume reduction system 260 can relax into a non-straight configuration, for example into a tapered helical coil. The catheter 120, or a separate tool, can deform the volume reduction system 260 as or after the volume reduction 260 exits the catheter 120. As shown by arrow 402, the catheter 120 can be partially translated away from the deploying volume reduction system 260, as the volume reduction system 260 exits the catheter 120.

Figure 21:
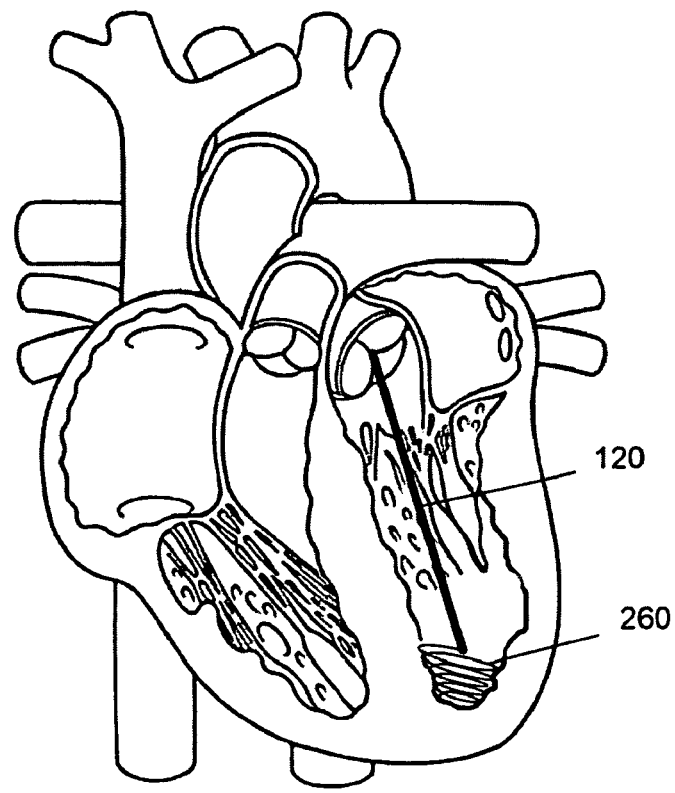

FIG. 21 illustrates that the volume deployment system 260 can fully exit the catheter 120 at a target site, for example the apex of the left ventricle. The catheter 120, and/or other fluid delivery tool, can be in fluid communication with the filling port 122.

Figure 22:
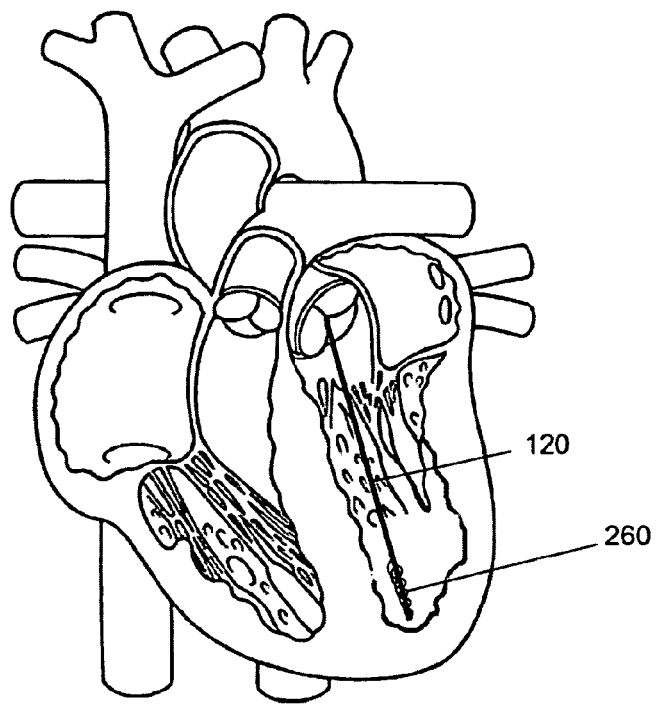
FIGS. 22 and 23 illustrate a variation of a method for deploying a variation of the volume reduction system in the left ventricle.

FIG. 22 illustrates that the volume deployment system 260 can be separatably attached to the outside of the catheter 120. For example, the volume deployment system 260 can be tightly wound around the catheter 120 and attached by one or more remotely controlled latches. The catheter 120 can be positioned at the target site to locate the volume reduction system 260 in the target site.

Figure 23:
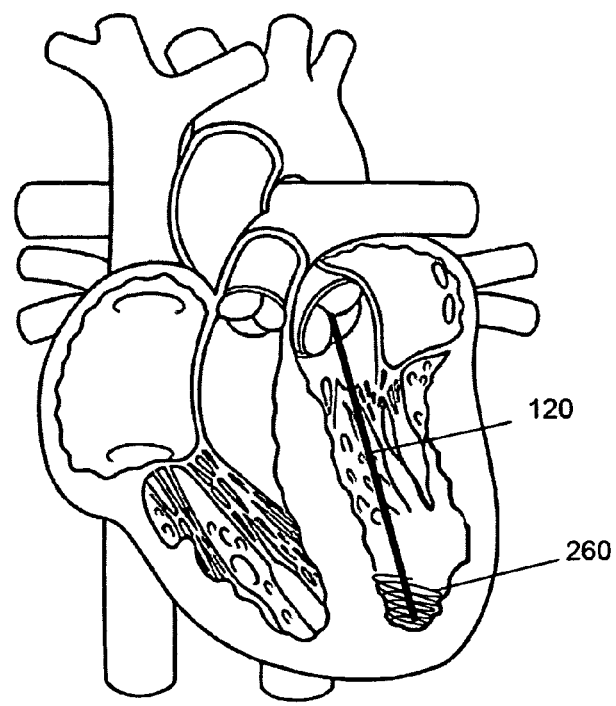

FIG. 23 illustrates that the volume reduction system 260 can be released from the catheter 120 at the target site, for example in the apex of the left ventricle. The catheter 120, and/or other fluid delivery tool, can be in fluid communication with the filling port 122.

Figure 24:
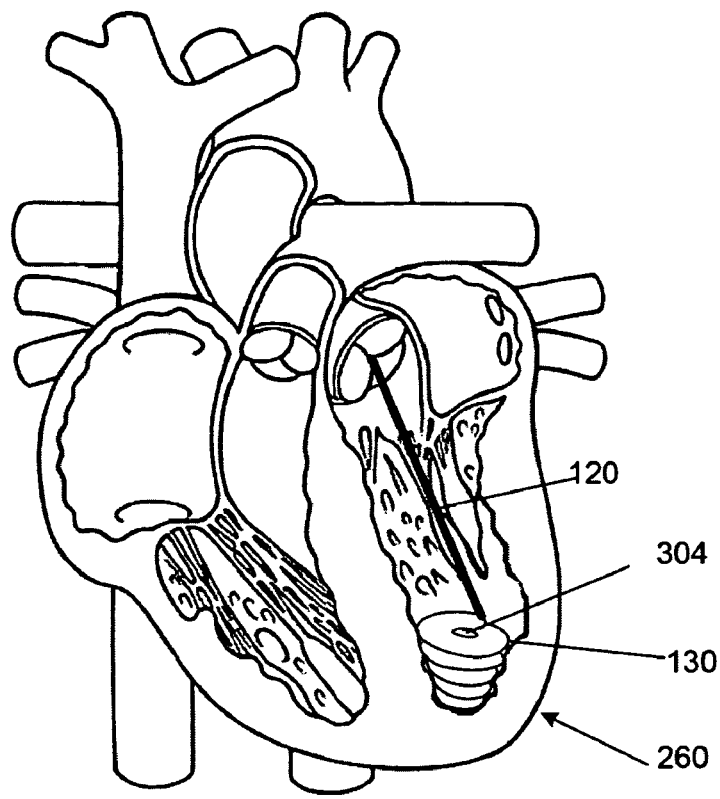
FIG. 24 illustrates a variation of a method for inflating a variation of the volume reduction system in the left ventricle.

FIG. 24 illustrates that fluid can be delivered to the containment system 130. The containment system 130 can inflate, for example, filling a substantial volume at the apex of the left ventricle.

Figure 25:
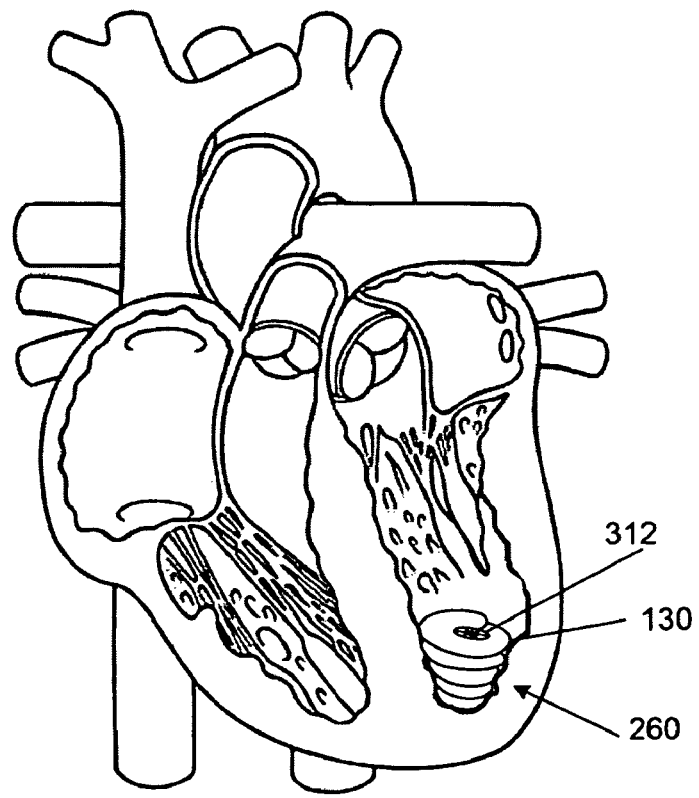
FIG. 25 illustrates a method of using a variation of the volume reduction system in the left ventricle.

FIG. 25 illustrates that the cover 312 can be attached at least covering the central port 304. The catheter 120 can be removed. The volume reduction system 260 can have radial hooks, anchors or barbs (not shown in FIG. 25). The hooks, barbs or anchors can deploy (or passively be previously deployed) into the surrounding tissue.

Figure 26:
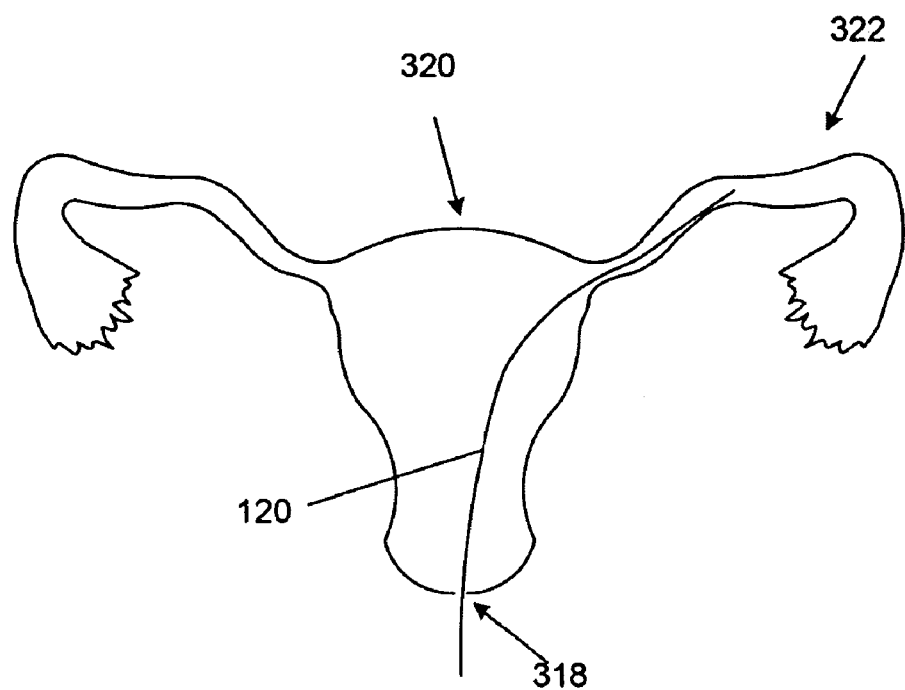
FIGS. 26 through 29 illustrate a variation of a method for deploying a volume reduction system in a fallopian tube, for example, for sterilization.
Figure 27:
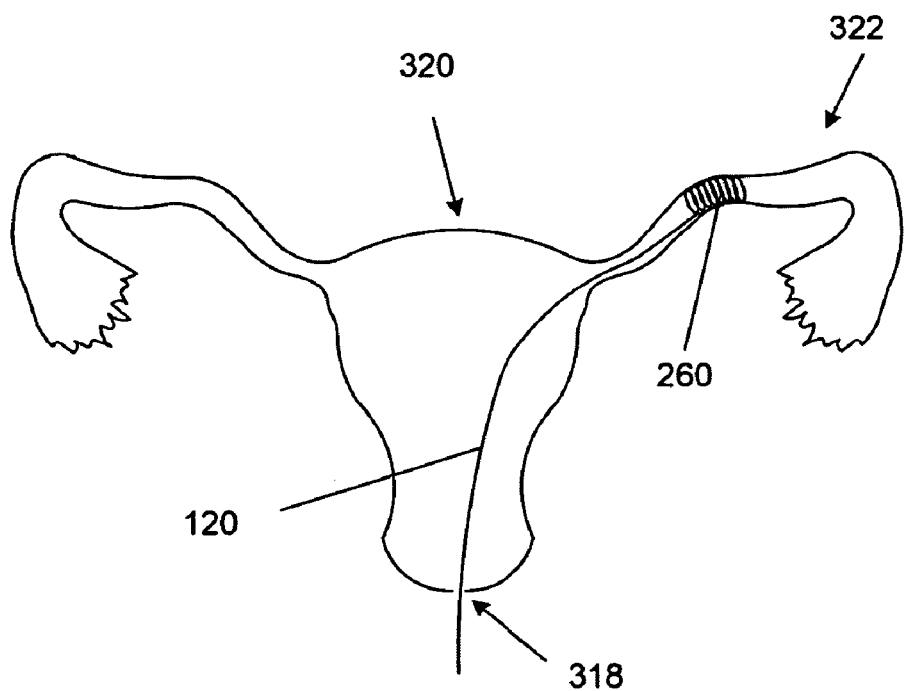

FIG. 26 illustrates that the catheter 120 can be positioned through an os 318 and uterus 320 and into a fallopian tube 322. FIG. 27 illustrates that the volume reduction device 260 can exit or be otherwise released from the catheter 120 in the fallopian tube.

Figure 28:
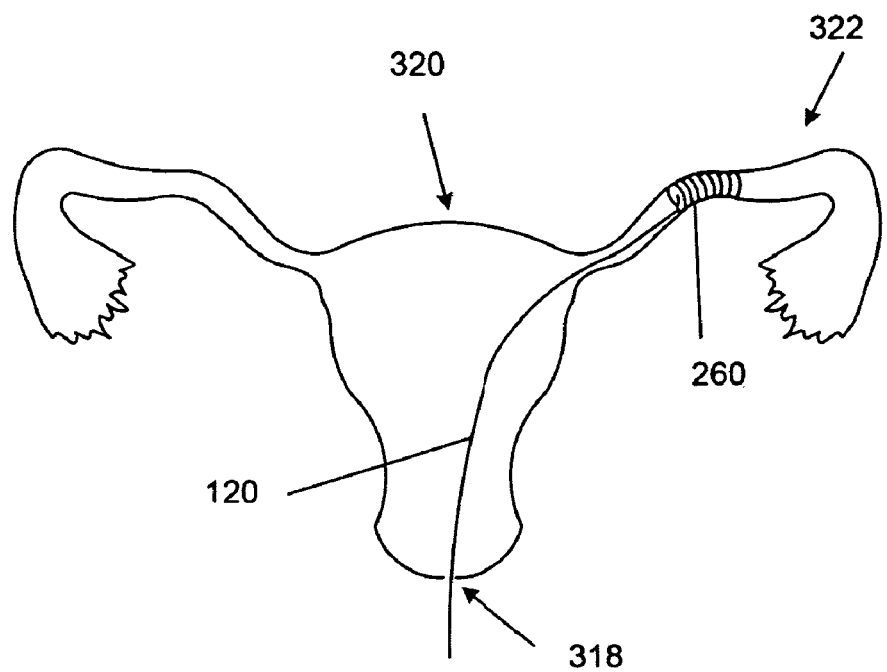

FIG. 28 illustrates that the volume reduction system 260 can be inflated or otherwise expanded. The volume reduction system 260 can be configured with no central port 304 (whether used in the fallopian tubes 322 or elsewhere). The volume reduction system 260 can be sufficiently inflated and/or sealed with the cover 312 to prevent transmission of sperm through the volume reduction system 260.

Figure 29:
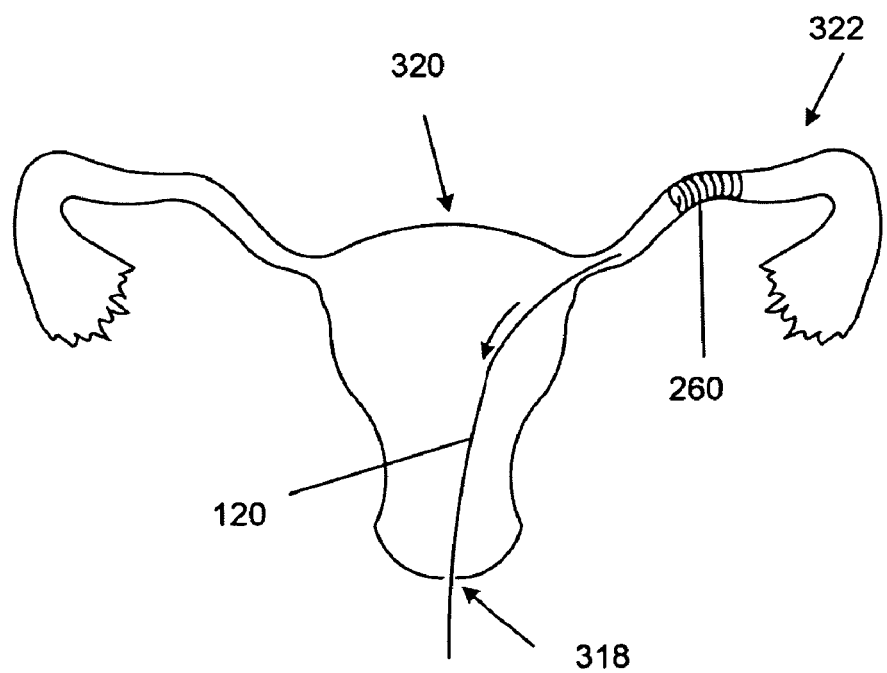

FIG. 29 illustrates that the catheter 120 can be detached from the volume reduction system 260 and removed, as shown by arrow, from the fallopian tube 322, uterus 320 and os 318.

Figure 30:
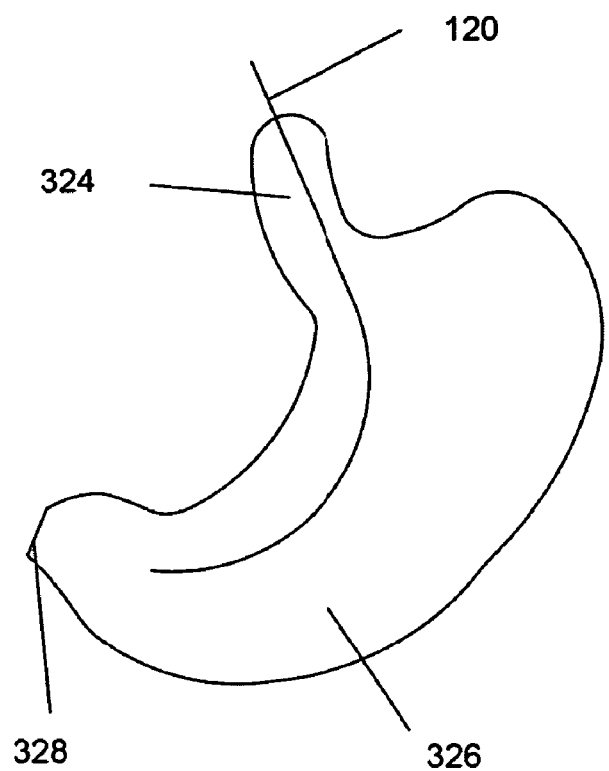
FIGS. 30 through 33 illustrate a variation of a method for deploying a volume reduction system in a fallopian tube, for example, for digestion control and/or appetite suppression.

FIG. 30 illustrates that the catheter 120 can be positioned through the esophagus 324 and into the stomach 326, for example before reaching the pyloric sphincter 328.

Figure 31:
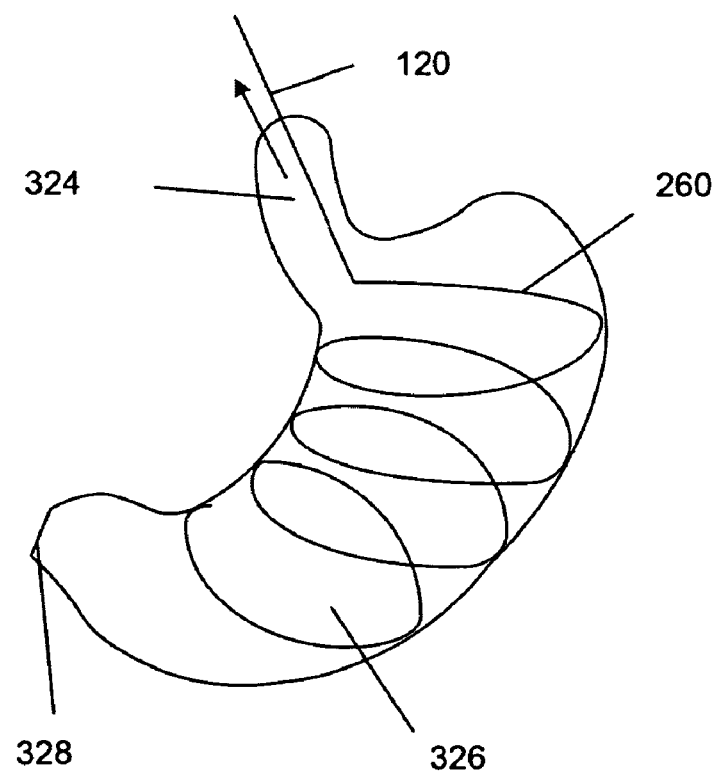

FIG. 31 illustrates that the volume reduction system 260 can be deployed from the catheter 120 by a method disclosed elsewhere herein. The volume reduction system can be generally configured as a spiral or helix around a partial or total length of the inner surface of the stomach 326.

Figure 32:
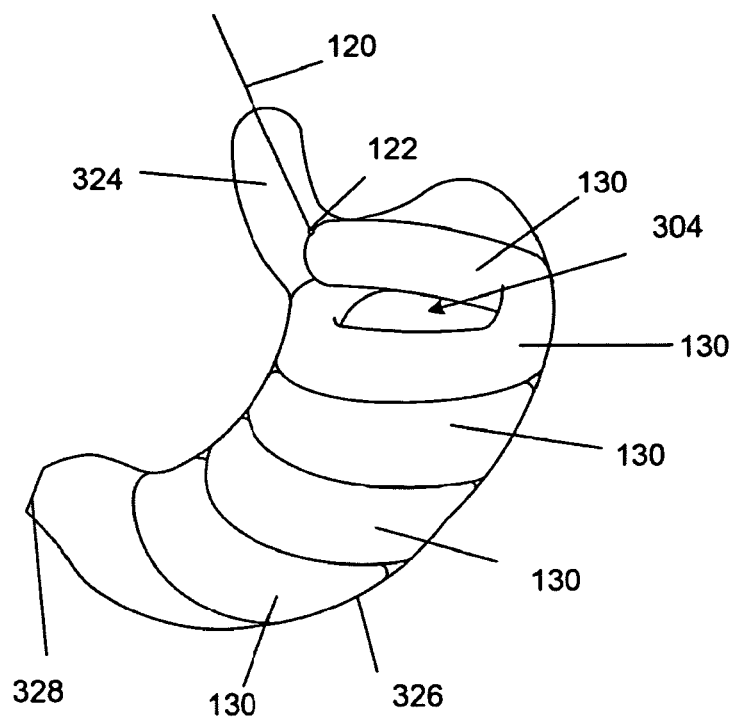

FIG. 32 illustrates that the catheter 120 or a separate fluid delivery tool can deliver fluid to the filling port 122. The containment system 130 can inflate or otherwise expand in the stomach 326. The containment system 130 can have the center port 304.

Figure 33:
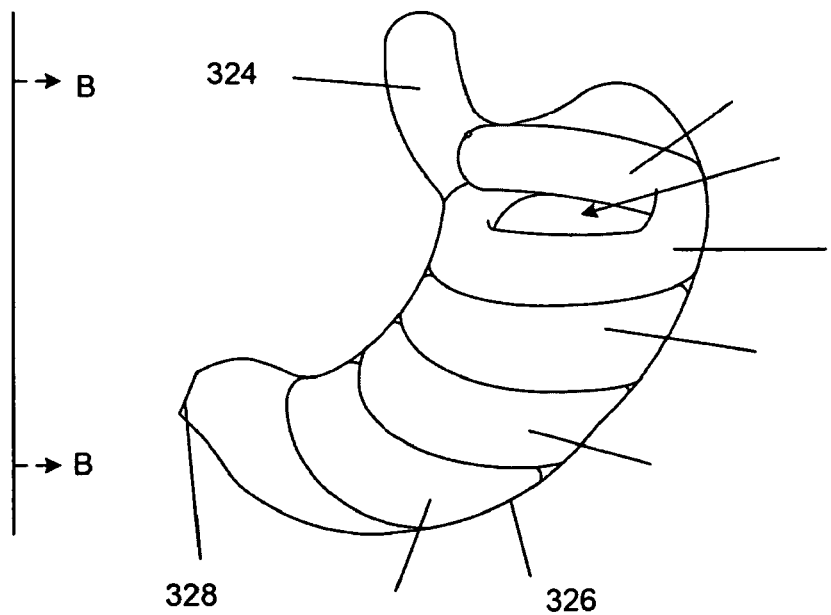

FIG. 33 illustrates that the catheter 120 and/or separate fluid delivery tool can be detached from the filling port 122 and/or the remainder of the volume reduction system 260. The filling port 122 can be actively or passively sealed.

Figure 34:
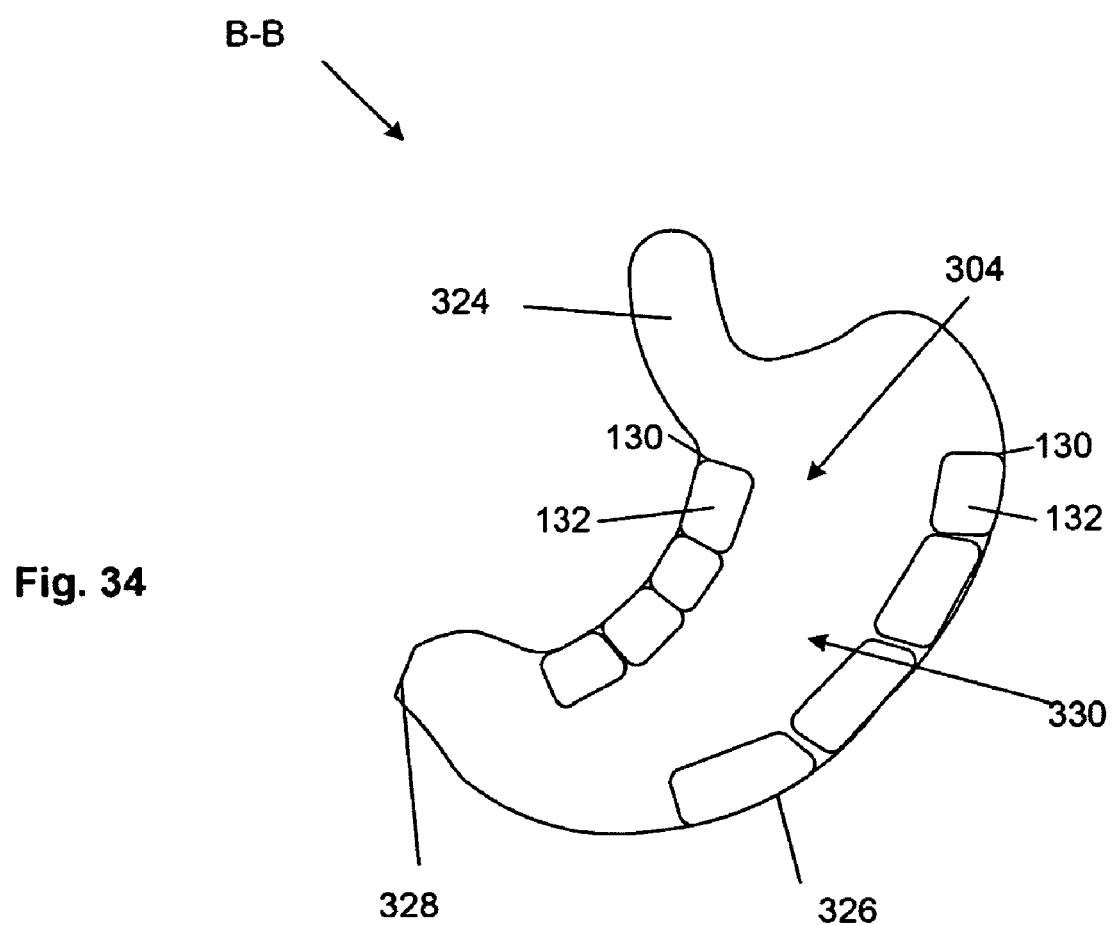
FIG. 34 illustrates a variation of cross-section B-B of FIG. 33.

FIG. 34 illustrates that the central port 304 can be in fluid communication with a central conduit 330. The central conduit 330 can permit material (e.g., food, fluid) to flow through the stomach 326. The containment system 130 can block a portion of the stomach surface from substantially interacting with contents of the stomach 326. The containment system 130 can occupy volume in the stomach 326.

The volume reduction system 260 can be removed from the target site, for example the fallopian tube 322, ventricle, or stomach. The volume reduction system 260 can be removed, for example by forcible removal, by draining or otherwise contracting and then translating, or combinations thereof. One or more holes can be drilled through the volume reduction system 260 and/or the cover can be removed, for example to reverse sterilization caused by deployment in the fallopian tubes 322.

Inflation, of the volume reduction system 260 in vivo can partially or completely occur due to absorption of bodily fluids. For example, the volume reduction system 260 can be made from polypropylene.

It is apparent to one skilled in the art that various changes and modifications can be made to this disclosure, and equivalents employed, without departing from the spirit and scope of the invention. Elements shown with any variation are exemplary for the specific variation and can be used on or in combination with any other variation within this disclosure.

What is claimed is:

1. A ventricular chamber volume reduction system, wherein the ventricular chamber has an apex and a wall, comprising:
    a frame comprising an anchor radially extending from the frame;
    a containment device deliverable through an intravascular catheter into a ventricular chamber and expandable from a collapsed shape to a helical filled shape once delivered into the ventricular chamber; and
    a filler within the containment device, wherein the filler expands the containment device from the collapsed shape to the filled shape; and
    wherein the containment device is configured to fit to the contour of the ventricular chamber wall extending from the apex of the ventricular chamber to the surface of the containment device farthest away from the apex, and wherein the containment device is configured to substantially fill the volume between the surface of the containment device farthest away from the apex and the apex.

2. The system of claim 1, further comprising a partition, wherein the partition is adjacent to the containment device, wherein the partition is positioned on the side of the containment device away from the apex.

3. The system of claim 2, wherein the partition is resilient.

4. The system of claim 1, wherein the containment device comprises a substantially conical configuration.

5. The system of claim 1, wherein the filler is curable.

6. The system of claim 1, wherein the filler comprises a polymer.

7. The system of claim 6, wherein the polymer is hydrophilic.

8. The system of claim 1, wherein the filler is delivered by a catheter.

9. The system of claim 1, further comprising attachment mechanisms that affix the containment device to a wall of the ventricular chamber.

10. The system of claim 1, further comprising a fillport for the containment device.

11. A ventricular chamber volume reduction system, comprising:
    a frame comprising an anchor extending radially from the frame;
    a container body deliverable into a portion of a ventricular chamber, and wherein the container body is expandable from a first shape to a helical second shape when delivered into the ventricular chamber, the container body having a tissue surface in contact with a wall of the ventricular chamber and an exposed surface facing into the volume of the ventricular chamber not occupied by the container body, and wherein the exposed surface substantially spans across the ventricular chamber, wherein the container body comprises a fillport, and wherein the container body is attached to the frame,
    wherein the second shape of the container body occupies substantially all of the space in the ventricular chamber between the wall of the portion of the ventricular chamber and the exposed surface, and wherein the second shape of the container body is in contact with the wall from the apex of the ventricular chamber to the surface of the container farthest away from the apex, thereby reducing ventricular volume exposed to a flow of blood.

12. The system of claim 11, further comprising a partition, wherein the partition is positioned on the side of the container adjacent to the exposed surface.

13. The system of claim 11, wherein the container body comprises an attachment device that affixes the tissue surface to the wall of the ventricular chamber.

14. A ventricular chamber volume reduction system, comprising:
    a frame comprising an anchor extending radially from the frame;
    a partition sequestering a portion of a ventricular chamber, thereby substantially removing the portion from a flow path for blood flowing within the ventricular chamber, the partition having an exposed surface facing the flow path, wherein placement of the partition decreases volume of blood flowing along the flow path within the ventricular chamber, and wherein the partition is resilient; and a fillable helical container volume having a substantially open central port, the container volume configured to be positioned between the partition and the apex portion of the ventricular chamber, wherein the container is configured to contact the wall of the ventricular chamber from the apex extending to the terminal end of the container adjacent to the partition, and wherein the container is configured to allow the resilient movement of the partition within the central port.

15. The system of claim 14, wherein the partition is attached to the fillable container.

16. The system of claim 14, wherein the partition is configured to be attached to a tissue surface of the wall of the ventricular chamber.

17. The system of claim 14, wherein the partition comprises with an antithrombogenic material.

18. The system of claim 14, wherein the partition further comprises a support to secure the position of the partition within the ventricular chamber.

19. The system of claim 14, wherein the partition is configured to absorb mechanical energy during diastole and emit mechanical energy during systole.

20. The system of claim 14, wherein the helical configuration of the container is spaced to allow for resilient motion of the container volume.

21. The system of claim 14, wherein the container volume comprises fingers extending from the remainder of the container volume, wherein the fingers are spaced apart to allow for resilient motion of the container volume.

* * * * *